(12) United States Patent
Baek et al.

(10) Patent No.: US 11,208,433 B2
(45) Date of Patent: Dec. 28, 2021

(54) PEPTIDE FOR INHIBITING SKIN INFLAMMATION AND COMPOSITION FOR PREVENTING OR TREATING SKIN INFLAMMATION CONTAINING THE SAME

(71) Applicant: AVIXGEN Inc., Seoul (KR)

(72) Inventors: Yi Yong Baek, Goyang-si (KR); Jun Sub Choi, Yongin-si (KR); Hye Cheong Koo, Gwangmyeong-si (KR)

(73) Assignee: AVIXGEN Inc., Seoul (KR)

( * ) Notice: Subject to any disclaimer, the term of this patent is extended or adjusted under 35 U.S.C. 154(b) by 0 days.

(21) Appl. No.: 16/346,861

(22) PCT Filed: Dec. 17, 2018

(86) PCT No.: PCT/KR2018/015999
§ 371 (c)(1),
(2) Date: May 1, 2019

(87) PCT Pub. No.: WO2019/132351
PCT Pub. Date: Jul. 4, 2019

(65) Prior Publication Data
US 2020/0190141 A1    Jun. 18, 2020

(30) Foreign Application Priority Data

Dec. 28, 2017    (KR) .................. 10-2017-0183165

(51) Int. Cl.
| | |
|---|---|
| C07K 5/11 | (2006.01) |
| A61K 8/64 | (2006.01) |
| A61Q 19/00 | (2006.01) |
| A61P 17/00 | (2006.01) |
| A61K 9/00 | (2006.01) |
| A61K 45/00 | (2006.01) |
| A61K 38/00 | (2006.01) |

(52) U.S. Cl.
CPC .............. *C07K 5/1019* (2013.01); *A61K 8/64* (2013.01); *A61K 9/0014* (2013.01); *A61P 17/00* (2018.01); *A61Q 19/00* (2013.01); *A61K 38/00* (2013.01); *A61K 45/00* (2013.01)

(58) Field of Classification Search
None
See application file for complete search history.

(56) References Cited

U.S. PATENT DOCUMENTS

| | | | | |
|---|---|---|---|---|
| 9,969,771 | B2 * | 5/2018 | Kim .................. | C07K 5/1019 |
| 2006/0063149 | A1 | 3/2006 | Berthet et al. | |
| 2007/0099276 | A1 | 5/2007 | Ott | |
| 2011/0268679 | A1 | 11/2011 | Sherris | |
| 2015/0266939 | A1 | 9/2015 | Vogan et al. | |
| 2017/0037083 | A1 * | 2/2017 | Kim .................. | C07K 5/1019 |

FOREIGN PATENT DOCUMENTS

| | | |
|---|---|---|
| AU | 2016366566 B | 6/2017 |
| CA | 2395539 A | 6/2001 |
| JP | H01224398 A1 | 9/1989 |
| JP | 2006-219435 A | 8/2006 |
| JP | 2008510019 A | 4/2008 |
| JP | 2009-527251 A | 7/2009 |
| JP | 2009528381 A | 8/2009 |
| JP | 2010512782 A | 4/2010 |
| KR | 1020110046961 A | 5/2011 |
| KR | 1020140033676 A | 3/2014 |
| KR | 10-1644440 B1 | 8/2016 |
| WO | 9320220 A1 | 10/1993 |
| WO | 1994017095 A | 8/1994 |
| WO | 199423751 A1 | 10/1994 |
| WO | 03060098 A2 | 7/2003 |
| WO | 2004-090544 A | 10/2004 |
| WO | 2005051419 A1 | 6/2005 |
| WO | 2006-056701 A | 6/2006 |
| WO | 2009033734 A2 | 3/2009 |
| WO | 2009139361 A | 11/2009 |
| WO | 2010-134537 A | 11/2010 |
| WO | 2012105467 A | 8/2012 |
| WO | 2012118092 A1 | 9/2012 |
| WO | 2013138795 A1 | 9/2013 |
| WO | WO-2018111051 A1 * | 6/2018 ............. C07K 19/00 |

OTHER PUBLICATIONS

Uniprot database search of Arg-Leu-Tyr-Gly conducted Mar. 16, 2020 (Year: 2020).*
Golden et al. "Chronic, not acute, skin-specific inflammation promotes thrombosis in psoriasis murine models," J Transl Med, 2015, vol. 13, pp. 382-391 (Year: 2015).*
Lund et al. "Lymphatic Vessels, Inflammation, and Immunity in Skin Cancer," Cancer Discovery, 2016, vol. 6, pp. 22-35 (Year: 216).*
Dinca et al. ("Intracellular Delivery of Proteins with Cell-Penetrating Peptides for Therapeutic Uses in Human Disease," Int. J. Mol. Sci. 2016, 17, 263, pp. 1-13) (Year: 2016).*
Groneberg et al., "Mast cells and vasculature in atopic dermatitis—potential stimulus of neoangiogenesis", Allergy, 2005, vol. 60, pp. 90-97.
"gag protein, partial [Human immunodeficiency virus 1]", GenBank: ACO49279.1, 2016, 1 page.
International Search Report for International Application No. PCT/KR2018/015999 (5 Pages) (dated Mar. 18, 2019).
NCBI Reference Sequence: NP_687035.1: GAG-POL [Simian immunodeficiency virus], Feb. 2013.

(Continued)

*Primary Examiner* — Christina Bradley
(74) *Attorney, Agent, or Firm* — Lucas & Mercanti, LLP

(57) ABSTRACT

The present invention relates to a peptide for inhibiting skin inflammation and a pharmaceutical composition and a cosmetic composition for preventing or treating skin inflammation including the same. Since the peptide, pharmaceutical composition and cosmetic composition are effective for improving symptoms of skin inflammation caused by atopic dermatitis and the like, they are useful for preventing, improving or treating skin inflammation.

8 Claims, 19 Drawing Sheets

Specification includes a Sequence Listing.

(56) References Cited

OTHER PUBLICATIONS

Genbank, AMK06423.1: Putative gag-pro-pol polyprotein [Murine leukemia virus], Feb. 2016.
PDB:2L44_A: Chain A, C-Terminal Zinc Knuckle Of The Hivncp7, Oct. 2012.
PDB: 2IHX_A: Chain A, Solution Structure Of The Rous Sarcoma Virus Nucleocapsid Protein:upsi Rna Packaging Signal Complex, Oct. 2012.
Gaj et al., "Protein delivery using Cys2-His2 zinc-finger domains", ACS Chemical Biology, 2014, vol. 9, pp. 1662-1667.
International Search Report dated Mar. 22, 2018 for Corresponding International Application No. PCT/KR2017/014897 ( 2 pages).
Dorfman, T. et al., 'Mapping of Functionally Important Residues of a Cysteine-Histidine Box in the Human Immunodeficiency Virus Type 1 Nucleocapsid Protein', Journal of Virology, 1993, pp. 6159-6169, vol. 67 No. 10.
Extended European Search Report for corresponding European Patent Application No. 17879807.0, dated Jun. 23, 2020, 7 pages.
Baek, YY. et al., "The tetrapeptide Arg-Leu-Tyr-Glu inhibits VEGF-induced angiogenesis" Biochem Biophys Res Commun. Aug. 7, 2015, pp. 532-537, vol. 463.
Mie Kristensen et al., "Applications and Challenges for Use of Cell-Penetrating Peptides as Delivery Vectors for Peptide and Protein Cargos", International Journal of Molecular Sciences, 2016, p. 185, vol. 17, No. 185.
Saman A. Nasrollahi et al., "Cell-penetrating Peptides as a Novel Transdermal Drug Delivery System", Chemical Biology & Drug Design, 2012, pp. 639-646, vol. 80, No. 5, XP055083780,ISSN: 1747-0277, DOI: 10.1111/cbdd.12008.
Ankur Gautam et al "Topical Delivery of Protein and Peptide Using Novel Cell Penetrating Peptide IMT-P8", Scientific Reports, 2016, pp. 1-13, vol. 6, No. 1, XP055684243, DOI: 10.1038/srep26278, Retrieved from the Internet: URL:http://www.nature.com/articles/srep26278.pdf.
Omichinski J G et al "Structural characterization of a 39-residuesynthetic peptide containing the two zinc binding domains from the HIV-1 p7 nucleocapsid protein by CD and NMR spectroscopy", FEBS Letters, Elsevier, Amsterdam, NL, 1991, pp. 25-30, XP028088512, ISSN: 0014-5793, DOI: 10.1016/0014-5793(91)80825-N.
Supplementary European Search Report for European patent application No. 18897048.7, dated Sep. 30, 2021, European Patent Office.

* cited by examiner

The day of first administration was designated as day 0.
Data are expressed as Mean ± S.D.
G1: Normal control, G2: Vehicle control, G3: Tetrapeptide, G4: ACP-Tetrapeptide, G5: Prednisolone The day of first administration was designated as day 0.
Data are expressed as Mean ± S.D.
G1: Normal control, G2: Vehicle control, G3: Tetrapeptide, G4: ACP-Tetrapeptide, G5: Prednisolone

*/ A significant difference at p<0.001/p<0.01 level compared to the G1
/## A significant difference at p<0.001/p<0.01 level compared to the G2

G1: Normal control, G2: Vehicle control, G3: Tetrapeptide,
G4: ACP-Tetrapeptide, G5: Prednisolone The day of first administration was designated as day 0.
Data are expressed as Mean ± S.D.
G1: Normal control, G2: Vehicle control, G3: Tetrapeptide, G4: ACP-Tetrapeptide, G5: Prednisolone
* A significant difference at p<0.05 level compared to the G1

The day of first administration was designated as day 0.
Data are expressed as Mean ± S.D.
G1: Normal control, G2: Vehicle control, G3: Tetrapeptide, G4: ACP-Tetrapeptide, G5: Prednisolone
* A significant difference at $p<0.05$ level compared to the G1

The day of first administration was designated as day 0.
Data are expressed as Mean ± S.D.
G1: Normal control, G2: Vehicle control, G3: Tetrapeptide, G4: ACP-Tetrapeptide, G5: Prednisolone
**/* A significant difference at $p<0.01/p<0.05$ level compared to the G1
A significant difference at $p<0.05$ level compared to the G2

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: tetrapeptide

<400> SEQUENCE: 1

Arg Leu Tyr Glu
1

<210> SEQ ID NO 2
<211> LENGTH: 39
<212> TYPE: PRT
<213> ORGANISM: Artificial Sequence
<220> FEATURE:
<223> OTHER INFORMATION: ACP

<400> SEQUENCE: 2

Val Lys Cys Phe Asn Cys Gly Lys Glu Gly His Thr Ala Arg Asn Cys
1               5                   10                  15

Arg Ala Pro Arg Lys Lys Gly Cys Trp Lys Cys Gly Lys Glu Gly His
            20                  25                  30

Gln Met Lys Asp Cys Thr Glu
        35

<210> SEQ ID NO 3
<211> LENGTH: 43
<212> TYPE: PRT
<213> ORGANISM: Artificial Sequence
<220> FEATURE:
<223> OTHER INFORMATION: ACP-tetrapeptide

<400> SEQUENCE: 3
```

```
Val Lys Cys Phe Asn Cys Gly Lys Glu Gly His Thr Ala Arg Asn Cys
1               5                   10                  15

Arg Ala Pro Arg Lys Lys Gly Cys Trp Lys Cys Gly Lys Glu Gly His
            20                  25                  30

Gln Met Lys Asp Cys Thr Glu Arg Leu Tyr Glu
        35                  40
```

PEPTIDE FOR INHIBITING SKIN INFLAMMATION AND COMPOSITION FOR PREVENTING OR TREATING SKIN INFLAMMATION CONTAINING THE SAME

CROSS-REFERENCE TO RELATED APPLICATIONS

This application is a 371 of PCT/KR2018/015999, filed on Dec. 17, 2018 which claims the benefit of Korean Patent Application No. 10-2017-0183165, filed Dec. 28, 2017 and the contents of each of which are incorporated herein by reference.

Statement Regarding Government Rights

The present invention has been made with the support of the Korean government under Grant Number HI17C2273 (Non-clinical research and development of new anti-retinal degenerative disease candidate substances) from the Ministry of Health and Welfare.

TECHNICAL FIELD

The present invention relates to a peptide for inhibiting skin inflammation and a pharmaceutical composition and a cosmetic composition for preventing or treating skin inflammation including the same.

BACKGROUND ART

Skin inflammation refers to a disease that causes a series of clinical signs and symptoms such as itching, edema, erythema and exfoliation due to various stimulating factors which cause a series of inflammatory reactions in the skin epithelium, which is known to include atopic dermatitis, contact dermatitis, seborrhea and acne, psoriasis, and the like.

Atopic dermatitis is a chronic inflammatory skin disease that occurs most often in infancy or childhood, and it repeatedly recovers and aggravates, which is accompanied by rash and severe itching due to external stimulants. The pathogenesis of atopic dermatitis has not yet been elucidated. However, pathological factors such as hyperactivity due to an IgE antibody increase or functional loss of T lymphocyte due to a cell-mediated immune functional decrease have been found, and thus it is thought to be a disease involving immunological abnormality. Further, it is reported that extrinsic atopic dermatitis, which occupies most of atopic dermatitis, is caused by IgE-related immune mechanism, and delay-type immune response due to T cell abnormality is involved rather than an immediate-type immune response to a specific allergen.

Currently, steroids and antihistamines are mainly used together with moisturizers in order to treat skin inflammation caused by atopic dermatitis and the like. However, steroids have anti-inflammatory or immunosuppressive properties, but their use is limited due to side effects. Further, antihistamines bind to histamine receptors on the surface of mast cells to inhibit the release of histamine. However, antihistamines' use is limited because they are ineffective in the production of various allergic-inflammatory mediators.

Meanwhile, drugs that inhibit the release of chemical mediators such as histamine and leukotriene from mast cells have been developed. Chromoglycic acid (Intal), tranilast (Rizaben) and the like are used as a drug for preventing or treating asthma, allergic rhinitis and atopic dermatitis. However, such synthetic products have a disadvantage in that they cannot be expected to provide the complete cure, they are not effective in long-term use, and they seriously cause systemic side effects.

Accordingly, the present inventors have completed the present invention by confirming that tetrapeptides inhibit skin inflammation without side effects.

DETAILED DESCRIPTION OF THE INVENTION

Technical Problem

An object of the present invention is to provide to a peptide for inhibiting skin inflammation, including an amino acid sequence represented by Arg-Leu-Tyr-Glu.

Another object of the present invention is to provide a pharmaceutical composition for preventing or treating skin inflammation including a peptide for inhibiting skin inflammation, including an amino acid sequence represented by Arg-Leu-Tyr-Glu.

Still another object of the present invention is to provide a cosmetic composition for preventing or improving skin inflammation including a peptide for inhibiting skin inflammation, including an amino acid sequence represented by Arg-Leu-Tyr-Glu.

Technical Solution

An aspect of the present invention provides a peptide for inhibiting skin inflammation, which includes an amino acid sequence represented by Arg-Leu-Tyr-Glu (SEQ ID NO: 1).

According to one embodiment of the present invention, the peptide may be one in which Arg is acetylated.

According to one embodiment of the present invention, the peptide may further include a cell penetrating peptide linked at an N-terminal or C-terminal thereof.

According to one embodiment of the present invention, the cell penetrating peptide may be any one selected from the group consisting of TAT, Antennapedia, VP22, Pep-1, polyarginine, poly-Lysine, Hph-1, Vectocell, Lactoferrin, Sim-2, LPIN3, 2IL-1a, and dNP2.

According to one embodiment of the present invention, the cell penetrating peptide may be a polypeptide including an amino acid sequence represented by SEQ ID NO: 2.

According to one embodiment of the present invention, the skin inflammation may be atopic dermatitis.

Another aspect of the present invention provides a pharmaceutical composition for preventing or treating skin inflammation, which includes the peptide for preventing skin inflammation including an amino acid sequence represented by Arg-Leu-Tyr-Glu (SEQ ID NO: 1) as an active ingredient.

According to one embodiment of the present invention, the composition may be in a formation of one selected from the group consisting of a gel, a paste, an ointment, a powder, an emulsion and an aerosol.

According to one embodiment of the present invention, the skin inflammation may be atopic dermatitis.

Yet another aspect of the present invention provides a cosmetic composition for preventing or improving skin inflammation, which includes the peptide including an amino acid sequence represented by Arg-Leu-Tyr-Glu (SEQ ID NO: 1) as an active ingredient.

According to one embodiment of the present invention, the skin inflammation may be atopic dermatitis.

Advantageous Effects

The peptide for inhibiting skin inflammation according to the present invention and the pharmaceutical composition and cosmetic composition for preventing or treating skin inflammation containing the same is effective for improving symptoms of skin inflammation caused by atopic dermatitis and the like, and thus they are useful for preventing, improving or treating skin inflammation.

BEST MODE

Figure 1:
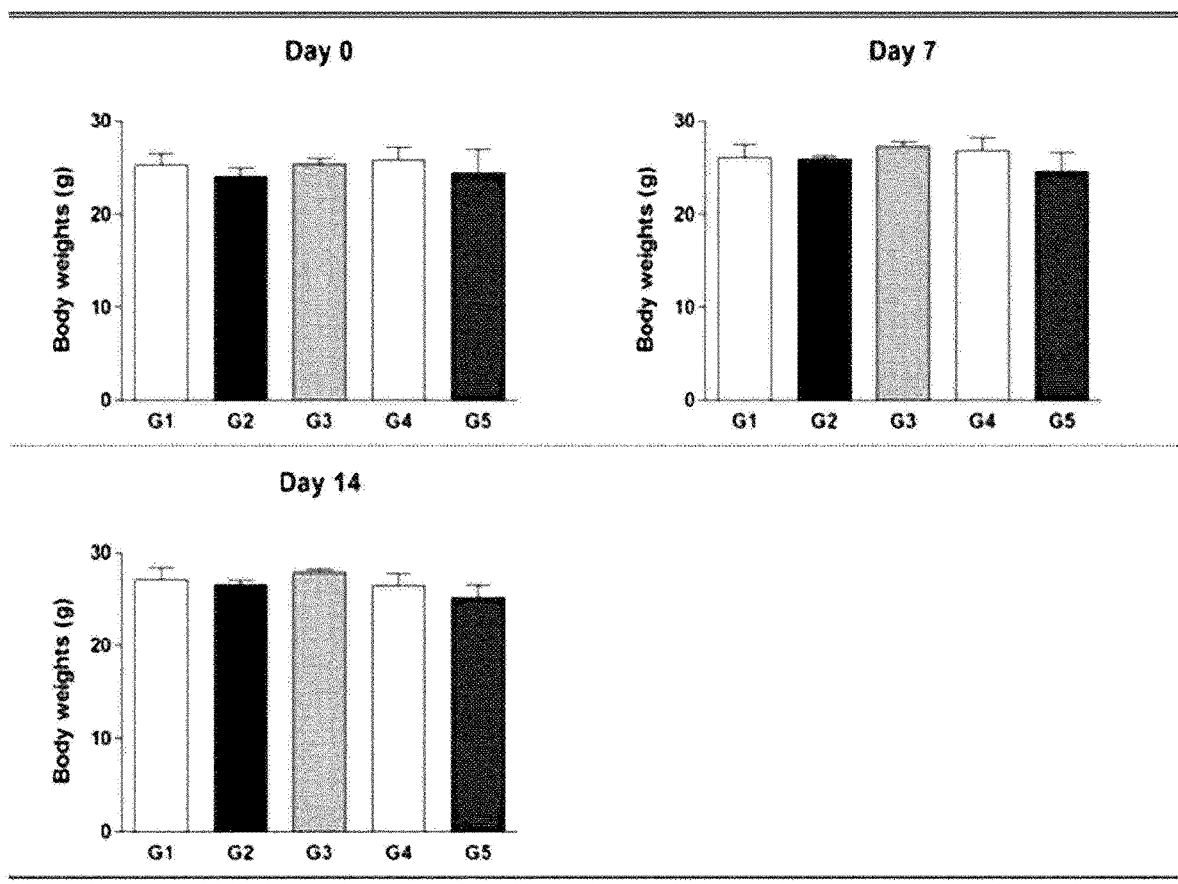
FIG. 1 is a graph illustrating changes in body weight of an animal model having the atopic dermatitis.

An aspect of the present invention provides a peptide for inhibiting skin inflammation, which includes an amino acid sequence represented by Arg-Leu-Tyr-Glu (SEQ ID NO: 1).

As used herein, the term "peptide" refers to a linear molecule which is formed by the manner in which the amino acid residues bind together by a peptide bond.

The tetrapeptide including the amino acid sequence represented by Arg-Leu-Tyr-Glu according to one embodiment of the present invention reduces IgE and histamine in blood, which are known as the cause of atopy for the skin and restores the tight junction-related proteins to inhibit the vascular barrier permeability. Further, when the tetrapeptide is treated even with a molecular ratio of at least 1000 times lower than that of prednisone, an anti-atopic agent, the tetrapeptide has the same level of effect as prednisone. Thus, it can be effectively used for preventing or treating skin inflammation caused by atopic dermatitis and the like.

According to one embodiment of the invention, the peptide may be acetylated at the N-terminus of SEQ ID NO: 1.

The tetrapeptide according to one embodiment of the invention is acetylated at the N-terminus of SEQ ID NO: 1, having effects of improving stability in blood and skin as compared with the non-acetylated tetrapeptide so that the prophylactic or therapeutic effect of skin inflammation can be sustained for a long time.

According to one embodiment of the invention, the peptide may further include a cell penetrating peptide linked at an N-terminal or C-terminal thereof.

As used herein, the term "N-terminus" refers to one of both terminal ends of the peptide molecule in which the amino group ($NH_2^-$) remains unbound, and generally refers to the left end of the amino acid sequence. The term "C-terminus" refers to one of both terminal ends of the peptide molecule in which the carboxyl group (COOH—) remains unbound and generally refers to the right end of the amino acid sequence. In the present invention, the cell-penetrating peptide is preferably linked to the $NH_2^-$ group of the N-terminal amino acid Arg of the amino acid of the tetrapeptide.

Meanwhile, as used herein, the term "cell penetrating peptide (CPP)" refers to a peptide which is capable of transferring a substance to be transported in vitro and/or in vivo such as a chemical substance, a small molecule, a polypeptide, and/or nucleic acids into cells. The cell penetrating peptide is a peptide having an amino acid sequence capable of passing through the cell membrane of the phospholipid bilayer itself. The tetrapeptide according to one embodiment of the present invention further includes a cell penetrating peptide sequence so that the tetrapeptide can be used on the skin surface where inflammation occurs.

According to one embodiment of the invention, the cell penetrating peptide may, but is not limited to, be any one selected from the group consisting of TAT, Antennapedia, VP22, Pep-1, polyarginine, poly-Lysine, Hph-1, Vectocell, Lactoferrin, Sim-2, LPIN3, 2IL-1a, and dNP2. Further, the cell penetrating peptide may be a polypeptide including an amino acid sequence represented by SEQ ID NO: 2.

According to one embodiment of the invention, the skin inflammation may be atopic dermatitis.

Another aspect of the present invention provides a pharmaceutical composition for preventing or treating skin inflammation, which includes the peptide for preventing skin inflammation including an amino acid sequence represented by Arg-Leu-Tyr-Glu (SEQ ID NO: 1) as an active ingredient.

As used herein, the term "prevention" refers to reducing the incidence of skin inflammation and includes maintaining the condition in which symptoms of already-occurring skin inflammation are not worsened. As used herein, the term "treatment" means that the symptoms of skin inflammation are improved or beneficially altered.

The pharmaceutical composition according to one embodiment of the present invention may include a pharmaceutically acceptable carrier. The pharmaceutically acceptable carrier to be included in the pharmaceutical composition according to one embodiment of the present invention is one commonly used when prepared. It includes lactose, dextrose, sucrose, sorbitol, mannitol, trehalose, hyaluronic acid, starch, acacia rubber, calcium phosphate, alginate, gelatin, calcium silicate, microcrystalline cellulose, polyvinyl pyrrolidone, cellulose, water, syrup, methylcellulose, methyl hydroxybenzoate, propyl hydroxybenzoate, talc, magnesium stearate, minerals oil and the like, but are not limited thereto. The pharmaceutical composition according to one embodiment of the present invention may further include a lubricant, a wetting agent, a sweetener, a flavoring agent, an emulsifying agent, a suspending agent, a preservative, etc. in addition to the components as described above. The suitable pharmaceutically acceptable carrier and formulation are described in detail in Remington's Pharmaceutical Sciences (22th ed., 2013).

A pharmaceutical composition according to one embodiment of the present invention may be administered with one or more known substances that exhibit activity in skin inflammation. Further, the pharmaceutical composition according to one embodiment of the present invention can be used alone or in combination with methods using surgery, hormone therapy, drug treatment, and/or biological response modifier for treatment of skin inflammation.

The pharmaceutical composition of the present invention may include various bases and/or additives that are necessary and suitable for the production of the formulation, and may further include such a nonionic surfactant, a silicone polymer, an extender pigment, a fragrance, a preservative, a disinfectant, an oxidation stabilizer, an organic solvent, an ionic or nonionic thickener, a plasticizer, an antioxidant, a free radical scavenger, an opacifier, a stabilizer, an emollient, a silicone, an α-hydroxy acid, a defoamer, a moisturizer, vitamin, insect repellent, a fragrance, a preservative, a surfactant, an anti-inflammatory agent, a substance P antagonist, a filler, a polymer, a propellant, a basic or acidifying agent, or a coloring agent.

The pharmaceutical composition of the present invention can be administered parenterally, for example, transdermally.

The appropriate dosage of the pharmaceutical composition of the present invention may vary depending on factors such as the formulation method, administration method, patient's age, body weight, sex, pathological condition, food, administration time, administration route, excretion rate, and responsiveness. A preferred dosage of the pharmaceutical composition of the present invention is within the range of 0.001 mg/kg to 1000 mg/kg on the basis of an adult.

The pharmaceutical composition of the present invention can be administered in various formulations during parenteral administration. Examples of the liquid preparation may include a suspension, a solution, an emulsion, a syrup and the like. In addition to water, liquid, and paraffin which are commonly used simple diluents, various excipients such as a wetting agent, a sweetener, a fragrance, and a preservative may be included. According to one embodiment of the present invention, the composition may be a formulation selected from the group consisting of a gel, a paste, an ointment, a powder, an emulsion and an aerosol.

Yet another aspect of the present invention provides a cosmetic composition for preventing or improving skin inflammation, which includes the peptide for preventing skin inflammation as an active ingredient.

The cosmetic composition including the peptide for preventing skin inflammation according to one embodiment of the present invention may be provided as any solid, liquid or semi-solid formulation, such as multiple emulsions such as cream, emulsions of oil in water, silicone in water, emulsion, water in oil, silicone in water, water/oil/water-type or water/silicone/water-type emulsion, and oil/water/oil-type or silicone/water/silicone-type emulsion and multiple emulsions such as an anhydrous composition, an aqueous dispersion, an oil, a milk, a balsam, a foam, a lotion, a gel, a cream gel, a hydroalcoholic solution, a hydroglycolic solution, a coating agent, a soap, a shampoo, a softener, a serum, a polysaccharide membrane, an ointment, a mousse, a pomade, a powder, a stick, a pencil and a spray.

Further, the cosmetic composition including the peptide for preventing skin inflammation according to one embodiment of the present invention may be applied to other type of solid kits such as, for example, a wet towel, a hydrogel, an adhesive patch, a non-adhesive patch, a microelectronic patch or a face mask using techniques known to those skilled in the art. The cosmetic composition may be included in other cosmetic products such as, for example, a fluid foundation, a compact foundation, a makeup removal lotion, a makeup removal milk, a concealer, an eye shadow, a lipstick, a lip protector, a lip gloss and powder.

The cosmetic composition including the peptide for preventing skin inflammation according to one embodiment of the present invention may include substances that increase the percutaneous absorption of the peptide, for example, dimethyl sulfoxide, dimethylacetamide, dimethylformamide, surfactant, azone (1-dodecylazacycloheptan-2-one), alcohol, urea, ethoxydiglycol, acetone, propylene glycol or polyethylene glycol, but is not limited thereto. Further, for effective penetration of the peptide, the adjacent site to be treated may be applied by methods such as iontophoresis, ultrasound therapy, electroporation, microelectronic patching, mechanical pressure, osmotic pressure, obstruent therapy, microinjection, needle-free injection, for example, injection using oxygen pressure or any combination thereof.

MODE FOR INVENTION

Hereinafter, one or more embodiments are described in more detail by way of Examples. However, these Examples are intended to illustrate one or more embodiments, and the scope of the present invention is not limited to these Examples.

Experimental Method

1. Synthesis of Peptides and Experimental Substance

Peptides represented by SEQ ID NOS: 1 to 3 listed in Table 1 below were synthesized by the FMOC solid-phase method in Chempeptide (Shanghai, China). The synthesized peptides were purified and analyzed by reverse phase high-performance liquid chromatography (HPLC-20AP, Japan) using a C18 analysis RP column (Shiseido capcell pak) and identified by a mass spectrometer (SHIMADZU LCMS-2010 EV, Japan).

TABLE 1

| Name of peptide | SEQ ID NO | Amino acid sequence | Remarks |
|---|---|---|---|
| Tetrapeptide | SEQ ID NO 1 | RLYE | acetylation form |
| ACP | SEQ ID NO 2 | VKCFNCGKEGHTARNCRAPRKKGCWKCGKEG HQMKDCTE | — |
| ACP-tetrapeptide | SEQ ID NO 3 | VKCFNCGKEGHTARNCRAPRKKGCWKCGKEG HQMKDCTERLYE | non-acetylated form |

ACP (Avixgen's cell penetrating peptide) was used as a cell penetrating peptide, which was linked at the N-terminal of the tetrapeptide. Tetrapeptides and ACP-tetrapeptides were cryopreserved for subsequent experiments. Sorondo® tablets including prednisolone as an active ingredient were used as a positive control. These substances were dissolved in sterile injection solution (Korea Pharmaceutical Industry Co., Ltd.), which was an excipient. Then, they were diluted to the corresponding concentration and used for experiments.

2. Breeding and Distribution of Animal Models

Twenty of 4-week-old Nc/NgaSlc female mice (Japan SLC, Inc.) with an average weight (g) within ±20% were adapted to the farm with a temperature of 23±3° C., a relative humidity of 55±15%, a ventilation frequency of 10 to 20 times/hours, a lighting time of 12 hours (light on at 8:00 am to light off at 8:00 μm) and illuminance of 150 to 300 Lux and then were used in the experiment. During the adaptation, administration and observation period, each mouse was raised in a rabbit stainless steel farm box (W 500×L 800×H 500 mm) in one mouse per one bleeding box, and the feed and water were freely ingested.

The mice were determined to be healthy during the adaptation period, followed by weighing. The mice were randomly divided into groups according to the ranked weight so that the average weight of each group was distributed as uniformly as possible.

3. Production of Atopic Dermatitis Animal Model

After the ear auricle of the NC/Nga mouse was shaved with a razor, the epilating agent was applied in an appropriate amount for the complete depilation. After the epilating agent was wiped off, Then, 100 mg of the AD-inducing reagent shown in Table 2 as below was uniformly applied to the ear auricle using a micropipette tip, thereby inducing atopic dermatitis for the first time.

After shaving with a razor for necessary, 150 μL of a 4% SDS aqueous solution was uniformly applied to the ear auricle using a micropipette, dried with a cold air using a dryer, and air-dried for about 2 to 3 hours. Then, 100 mg of the same AD-inducing reagent was uniformly applied to the ear auricle using a micropipette tip, thereby inducing atopic dermatitis after 2 times. All treatments were carried out twice a week to be 6 times for a total of 3 weeks, thereby producing atopic dermatitis animal model.

TABLE 2

| Item | | |
|---|---|---|
| Origin | | Biostir ®AD Lot No. 1W2 Dermatophagoides farinae (house dust mite) |
| Composition | Protein | 79.5 mg/g Biostir ®AD |
| | Major Allergen, Derf 1 | 110.7 μg/g Biostir ®AD |
| | Major Allergen, Derf 2 | 42.9 μg/g Biostir ®AD |

TABLE 2-continued

| Property | Ointment |
|---|---|
| Storage | −20° C. |

4. Experimental Group Design of Atopic Dermatitis Animal Model

The experimental groups were divided into five groups, and each group includes four mice as shown in Table 3 below. Each group was treated as shown in Table 3 below. The mice of groups 2 to 5 were obtained by the atopic dermatitis animal model prepared in Experimental Method 3 as described above.

TABLE 3

| Groups | Induction of atopic dermatitis | Experimental substance | Dose (μg/ear) | Dose amount (μg/ear) |
|---|---|---|---|---|
| Group 1 (Normal control group) | N | — | — | 10 |
| Group 2 (Induced control group) | Y | — | — | 10 |
| Group 3 (Experimental group 1) | Y | Tetrapeptide | 0.622 | 10 |
| Group 4 (Experimental group 2) | Y | ACP-tetrapeptide | 4.987 | 10 |
| Group 5 (positive control) | Y | Prednisolone | 50 | 10 |

The experimental substance and the control substance were uniformly applied to the ear auricle using a micropipette tip. From the day of the experimental substance administration (Day 0) to the day of the autopsy (Day 14), they were administered once a day for 2 weeks.

5. Assessment Method of Atopic Dermatitis in Animal Models 5-1. Weight Measurement The mice were weighed at the day of group separation or on the day of starting the experimental substance administration. Subsequently, they were measured once a week and on the day of the autopsy.

5-2. Measurement of Ear Thickness and Photography

Ear thickness was measured for each individual by calipers, and the ear area was photographed. Ear thickness measurement and photographing were performed once a week on the day of starting the experimental substance administration and thereafter.

5-3. Visual Pathological Evaluation

For the visual pathological evaluation of atopic dermatitis, evaluation of skin clinical index (Matsuda et al., 1997) was performed at intervals of one week from the beginning of the onset of atopic dermatitis. For each individual, 0

(none), 1 (mild), 2 (moderate) and 3 (severe) were recorded for erythema/hemorrhage, edema, excoriation/erosion and scaling/dryness. Then, the scores of each item were combined, and the total score was used to determine the final grade.

5-4. ELISA Analysis

On the day of the autopsy, blood samples were collected from the abdominal vein using a syringe. The serum isolated from the blood was analyzed for IgE and histamine using an ELISA kit.

5-5. Histopathological Examination

On the day of the autopsy, ears were removed for the histopathological examination and fixed in 10% neutral buffered formalin solution. The fixed tissues were subject to the general tissue treatment such as reprofiling, dehydration, paraffin embedding, and dissection, thereby preparing specimens for histopathological examination. Then, hematoxylin and eosin (H & E) and TUNEL assays were performed on histopathologic specimens, and the light microscopy (Olympus BX53, Japan) was used to observe histopathologic changes. In the histopathologic evaluation using hematoxylin and eosin staining slides, in order to compare the degree of the lesion with the induced control group, the most severe lesion was selected, and then the hypertrophy, hyperkeratosis and infiltration by inflammatory cells were evaluated in the epidermis. In the dermis, the infiltration by inflammatory cells was evaluated. Scoring criteria are the same as 0 (no symptoms), 1 (mild), 2 (moderate), and 3 (severe) (Taniguchi Y et al 2003).

5-6. Angiogenic Markers, Inflammatory Cells Distribution and Keratin Analysis in Atopic Dermis Tissues According to Immunohistochemical Staining Atopy mouse skin tissues were immersed in Xylene three times for 5 minutes, 100% ethanol for 2 minutes, 95% ethanol for 2 minutes, 90% ethanol for 2 minutes, 70% ethanol for 2 minutes and D.W. for 2 minutes to remove paraffin and to perform hydration. After washing with PBS, they were treated with 0.2% Triton X-100 to increase cell permeability. After re-washing with PBS, they were reacted with blocking solution, 3% bovine serum albumin, for 1 hour. For inflammatory cells and keratin staining, they were reacted with F4/80 (sc-377009, Santa Cruz) and cytokeratin (NB600-579, NOVUSBIO) antibodies, respectively, at room temperature for 2 hours. After washing with PBS, they were treated with Texas Red (ab6787, Abcam) secondary antibody and reacted at room temperature for 60 minutes. The mounting solution was dropped on the tissue of the slide. Then, the tissue was covered with a cover slide, and the sample was observed under a fluorescence microscope. For analysis of the degree of angiogenesis, the atopic skin tissue was reacted with FITC-conjugated isolectin B4 (L2895, Sigma), a blood vessel marker at room temperature for 2 hours. The mounting solution was dropped on the tissue of the slide. Then, the tissue was covered with a cover slide, and the sample was observed under a fluorescence microscope The mouse skin tissues stained with the respective markers were photographed using a fluorescence microscope (DMil, Leica, Germany), and fluorescence intensities were quantitatively analyzed using an ImageJ program (NIH, Bethesda, Md., USA).

5-7. Statistical Analysis

Parametric multiple comparison procedures or non-parametric multiple comparison procedures were used for the results of these experiments. For the parametric multiple comparisons, the normality of the data was assumed, and the results were tested by parametric one-way ANOVA. If the results were significant, Dunnett's multiple comparison test was conducted to perform post-test to analyze the significant differences between the experimental groups. For nonparametric multiple comparisons, Kruskal-Wallis'H-test was used. If the results were significant, the significant differences between the experimental groups were analyzed using the Mann Whitney U-test, which is a post-test.

Statistical analysis was performed using Prism 5.03 (GraphPad Software Inc., San Diego, Calif., USA) and SPSS Statistics 18.0K. When a p-value is less than 0.05, it was considered statistically significant.

6. ACP-Tetrapeptide's Cell Membrane Permeation Experiment

HeLa cells were inoculated in a 12-well plate containing glass at a density of $1\times10^5$ cells/well and cultured for 24 hours to attach the cells to the glass. Then, HeLa cells were treated with 3 µM ACP-FITC peptide and 3, 15, and 30 µM ACP-tetrapeptide-FITC peptide for 3 hours. After 3 hours, the cells were washed three times with PBS. Then, the cells were fixed with 3.7% formaldehyde for 20 minutes and treated with PBS containing 0.2% Triton X-100 to increase cell permeability. Then, the cells were blocked with 3% BSA for 1 hour, reacted with a tubulin antibody (Santa Cruz Biotechnology, U.S.A.) at room temperature for 2 hours, and washed three times with PBS. Next, the cells were treated with a Cy3-conjugated secondary antibody (Jackson ImmunoResearch, USA) at room temperature for 1 hour, washed twice with PBS, and then stained with 4',6-diamidino-2-phenylindole (DAPI) for 10 minutes. Finally, the HeLa cell-attached glass was removed and mounted on a sliding glass. The cells were observed under a fluorescence microscope (DMil, Leica, Germany).

7. Experiment for Confirming Inhibition of Vascular Barrier Permeability Due to Vascular Barrier Breakdown by Tetrapeptide 7-1. Experiment for Confirming Inhibition of Improved Vascular Barrier Permeability Due to Vascular Barrier Breakdown by VEGF in HUVEC Human umbilical vein endothelial cells (HUVECs) were starved with M199 media supplemented with 1% FBS for 4 hours and then inoculated at the number of $1\times10^5$ in the transwell plate upper chamber. Since the three types of tetrapeptides used in these experiments have their different half-lives in serum, acetylated tetrapeptides, tetrapeptides in which Arg is a D-form and non-acetylated tetrapeptides were incubated in serum for 2 hours. Then, HUVECs were treated with those tetrapeptides. Each was treated with the peptides. After 30 minutes, they were treated with 20 ng/ml of vascular endothelial growth factor (VEGF) for 1 hour. After treating with [$^{14}$C] sucrose in the upper chamber at a concentration of 0.8 mCi/ml for 30 minutes, the radiation level of the lower compartment was measured using a liquid scintillation counter.

7-2. Experiment for Confirming Recovery of Tight Junction-Related Protein Broken by VEGF in HUVEC HUVECs were starved with M199 media supplemented with 1% FBS for 4 hours, inoculated on a 24-well plate containing glass at the number of $1\times10^5$ cells, and cultured for 24 hours to attach the cells to the glass. HUVECs were pretreated with the acetylated tetrapeptide and the non-acetylated tetrapeptide (—Ac) for 30 minutes and treated with VEGF at a concentration of 20 ng/ml for 1 hour. Thereafter, the cells were washed three times with PBS, fixed in 3.7% formaldehyde for 20 minutes, and treated with PBS containing 0.2% Triton X-100 to increase vascular permeability. After blocking with 3% BSA for 1 hour, they were reacted with VE-cadherin (adherens junction) and ZO-1 (tight junction) antibodies at room temperature for 2 hours and washed three times with PBS. They were treated with Cy3 secondary antibodies, reacted at room temperature for 1 hour, washed twice with PBS, and stained with DAPI for 10 minutes. The huvec-attached glass was removed and mounted on a sliding glass. The cells were observed with a confocal microscope.

Experiment Result

1. Confirmation of the Efficacy of Tetrapeptides in Atopic Dermatitis Animal Models 1-1. Confirmation of Weight Maintenance of Experimental Group As a result of measuring the weight of the mice according to the experimental method as described above, no statistically significant difference in body weight was observed among all the experimental groups during the entire experimental period (FIG. 1).

In other words, the above results indicate that the tetrapeptide does not affect body weight.

1-2. Confirmation of Ear Thickness Reduction Effect

Figure 2:
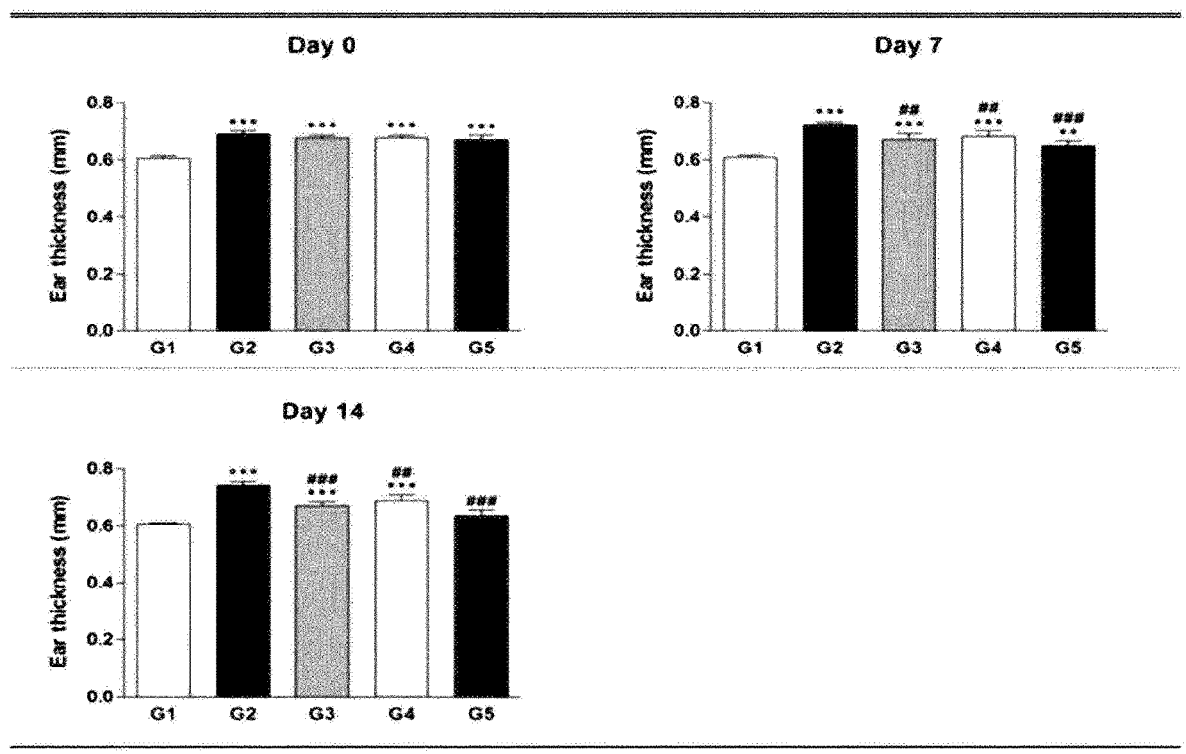
FIG. 2 is a graph illustrating changes in ear thickness of an animal model having the atopic dermatitis.
Figure 3:
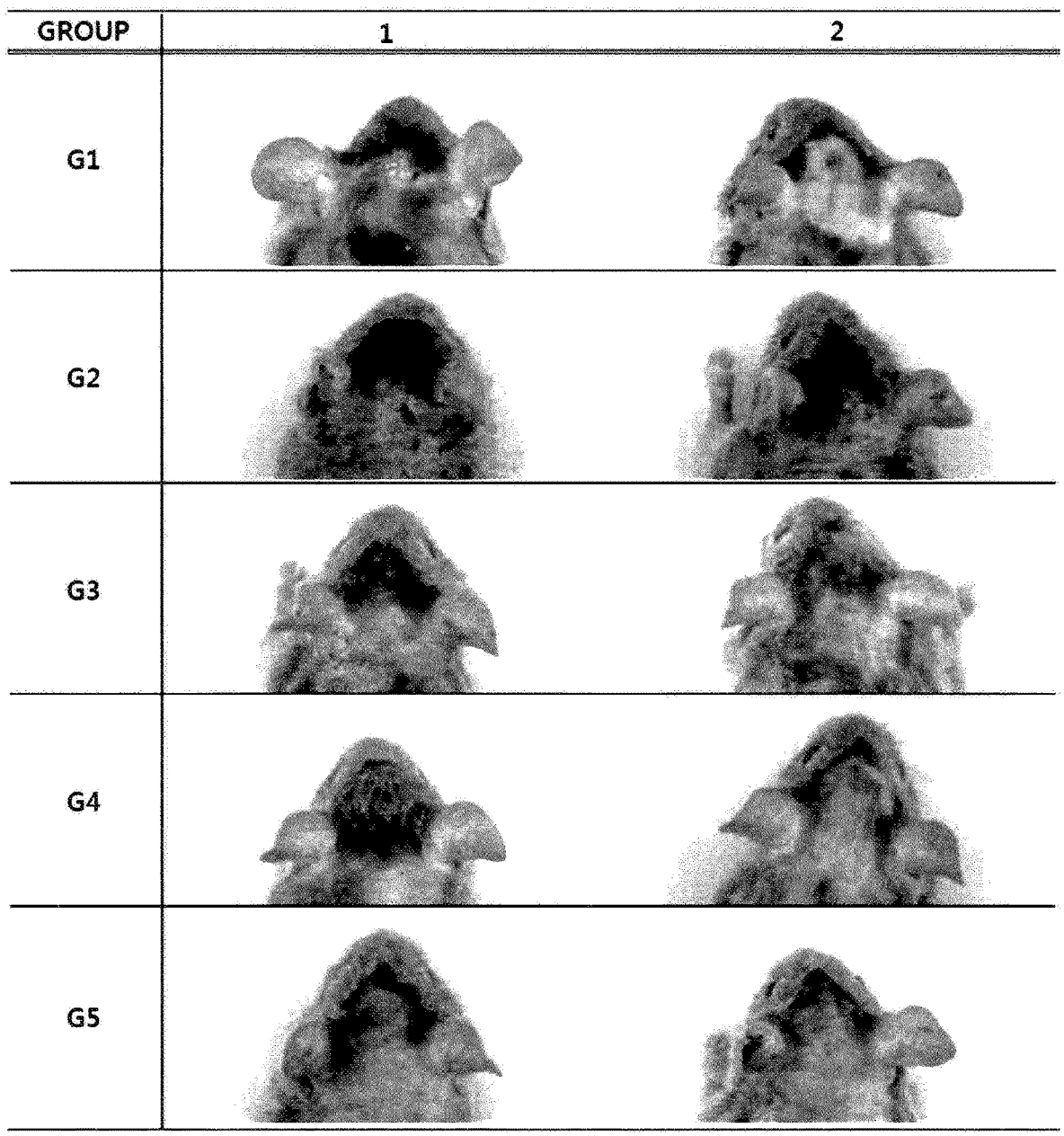
FIG. 3 is a photograph illustrating the results of visual pathology tests of the animal model groups 1 to 5 having the atopic dermatitis.

Ear thickness of all atopy-induced groups (groups 2 to 5) at 0 and 7 days after administration of the experimental substance was significantly thicker ($p<0.001$ or $p<0.01$) than that of the normal control group (group 1). On the 14th day after administration of the experimental substance, the ear thicknesses of the induced control group (group 2), the tetrapeptide treated group (group 3) and the ACP-tetrapeptide treated group (group 4) were significantly thicker than that of the group 1 ($p<0.001$). On the $7^{th}$ and $14^{th}$ day after administration of the experimental substance, ear thicknesses of group 3, group 4 and prednisone treated group (group 5) were significantly thinner ($p<0.001$ or $p<0.01$) than that of group (FIG. 2). The above results indicate that the tetrapeptide and ACP-tetrapeptide have an improvement effect on atopic dermatitis.

Figure 4:
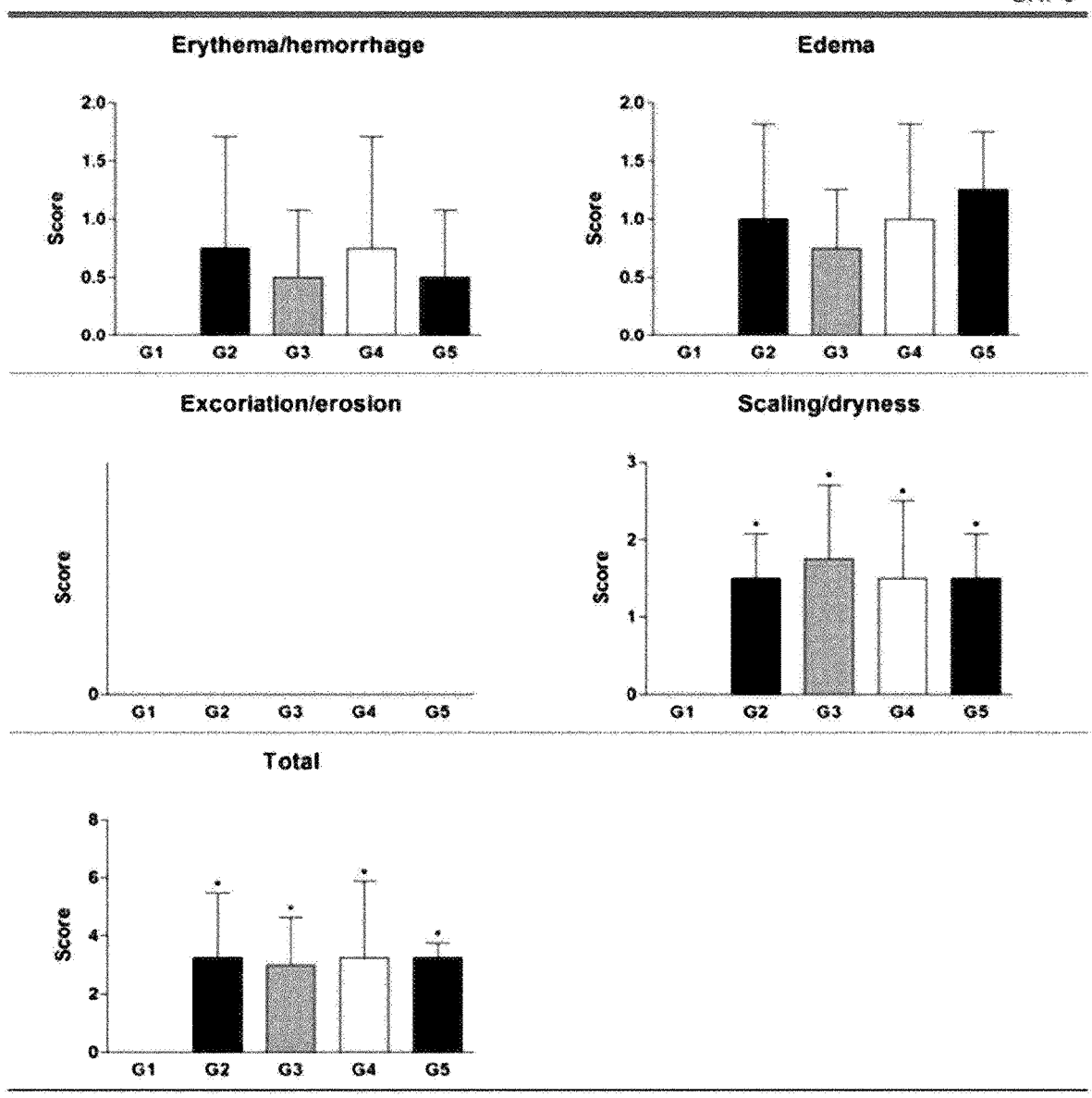
FIG. 4 is a graph illustrating erythema/hemorrhage, edema, excoriation/erosion, scaling/dryness, and total score on Day 0 according to visual pathological tests of the animal model having the atopic dermatitis.
Figure 5:
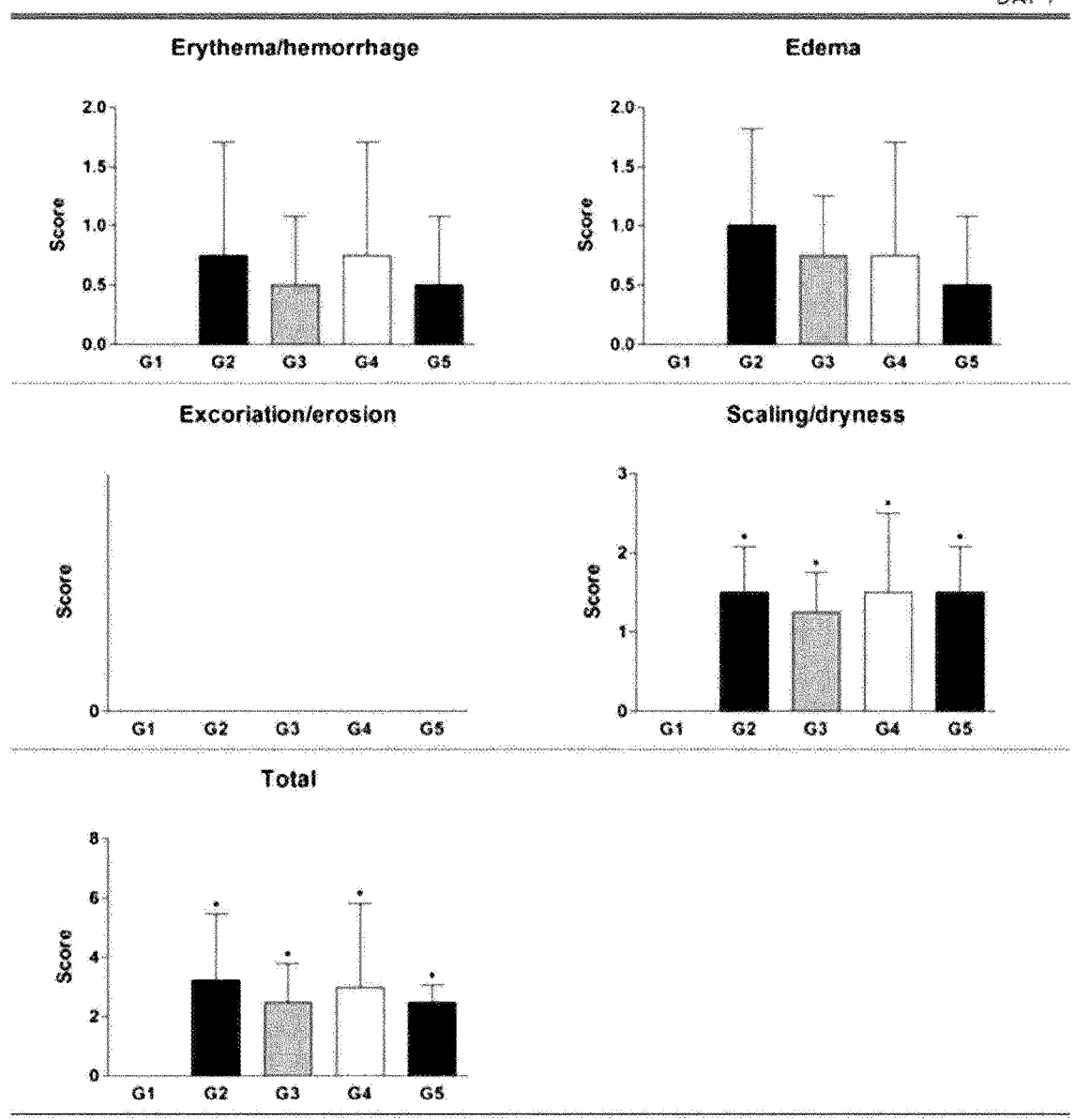
FIG. 5 is a graph illustrating erythema/hemorrhage, edema, excoriation/erosion, scaling/dryness, and total score on Day 7 according to visual pathological tests of the animal model having the atopic dermatitis.
Figure 6:
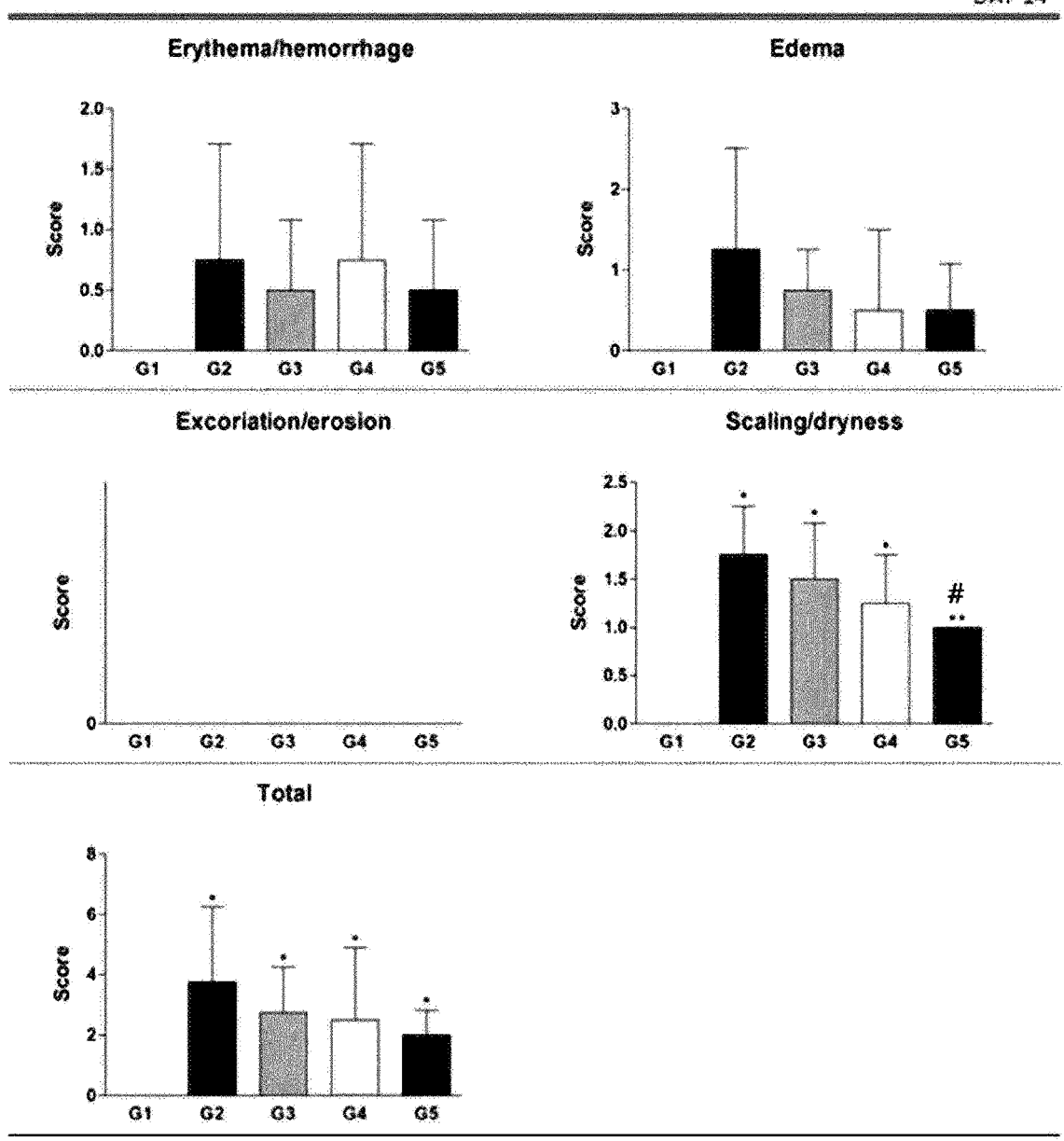
FIG. 6 is a graph illustrating erythema/hemorrhage, edema, excoriation/erosion, scaling/dryness, and total score on Day 14 according to visual pathological tests of the animal model having the atopic dermatitis.

1-3. Confirmation of the Improvement of Atopic Dermatitis by Visual Pathological Evaluation The scaling/dryness and total score levels of all atopy-induced groups were significantly higher than those of group 1 on 0 (FIG. 4), 7th (FIG. 5) and 14th (FIG. 6) days after administration of the experimental substance ($p<0.01$ or $p<0.05$), but the scaling/dryness level of group 5 was significantly lower than that of group 2 ($p<0.05$) on 14th day after administration of the experimental substance. In most of the items except scoring/dryness, there was no significant difference compared with the normal control group. However, in the case of the total score, the score levels of the tetrapeptide treated group and the ACP-tetrapeptide treated group were similar to that of the prednisolone treated group. The above results indicate that the tetrapeptide and ACP-tetrapeptide have an improvement effect on the symptoms of atopic dermatitis.

1-4. Confirmation of Reduction Effect on IgE and Histamine in Serum

Figure 7:
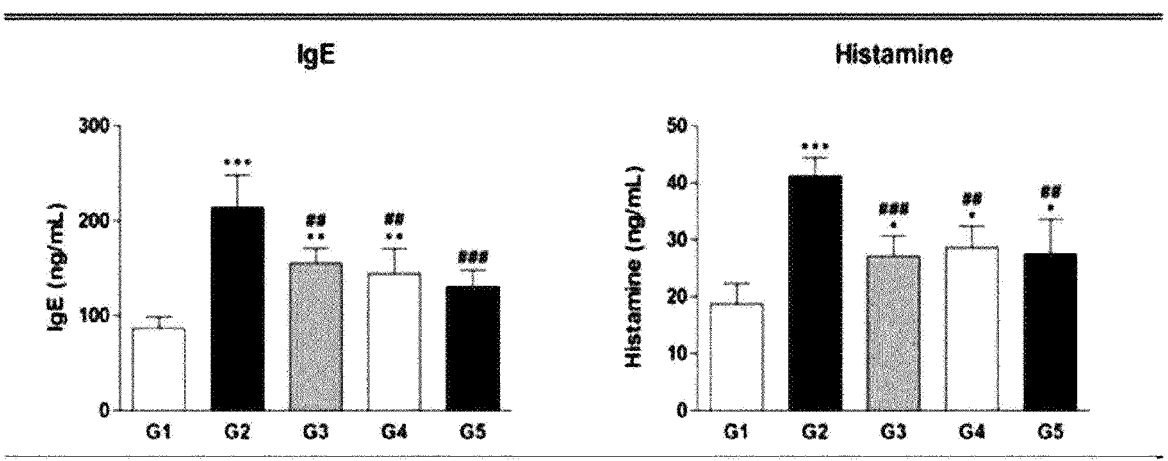
FIG. 7 is a graph illustrating the concentrations of IgE and histamine in blood according to ELISA analysis for each animal model group having the atopic dermatitis.

The IgE levels of group 2, group 3 and group 4 were significantly higher than that of the normal control group ($p<0.001$ or $p<0.01$). The histamine levels of all atopy-induced groups were significantly higher than that of group 1 ($P<0.001$ or $p<0.05$). The IgE and histamine levels of group 3, group 4 and group 5 were significantly lower than that of group 2 ($p<0.001$ or $p<0.01$) and lower than that of the prednisolone treated group (FIG. 7). The above results indicate that the tetrapeptide and ACP-tetrapeptide have an improvement effect on the symptoms of atopic dermatitis caused by overproduction of IgE and histamine.

Figure 8:
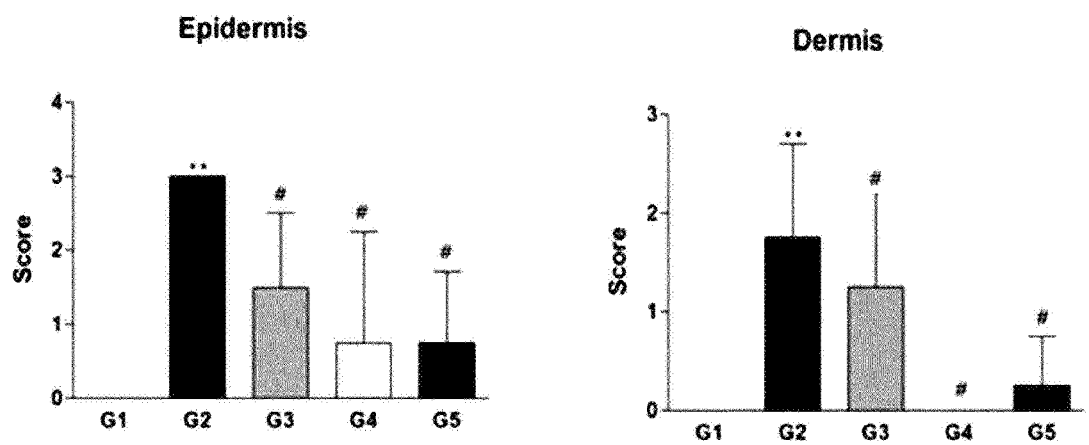
FIG. 8 is a graph illustrating scores of epidermis and dermis according to the histopathological test results for each animal model group having the atopic dermatitis.
Figure 9:
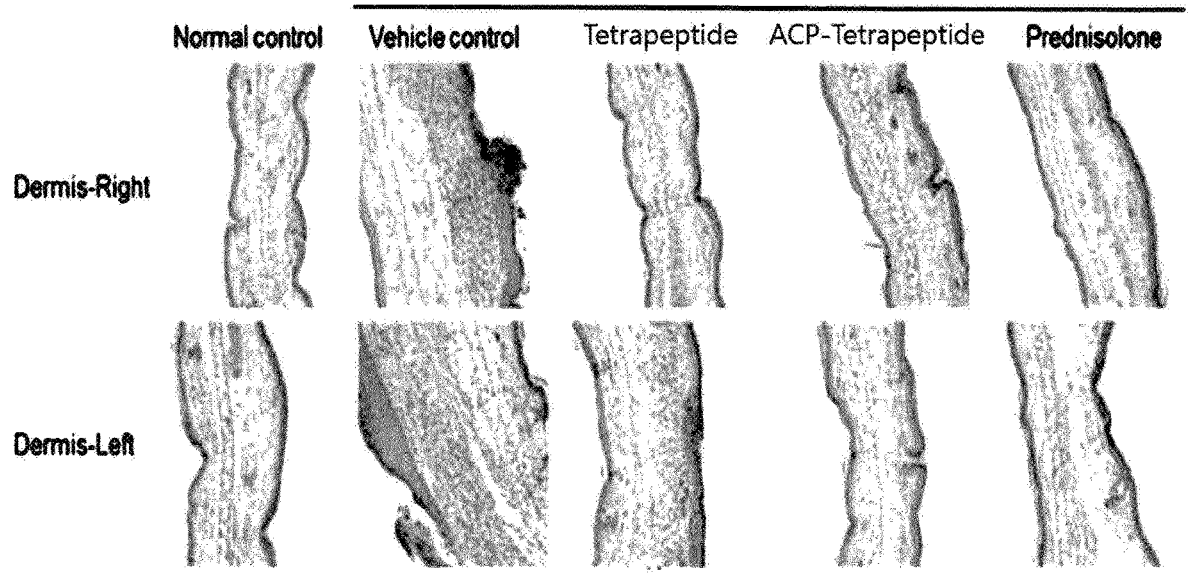
FIG. 9 is a photograph illustrating the epidermis and dermis for each animal model group having the atopic dermatitis.

1-5. Confirmation of Reduction Effect on Atopic Dermatitis in Epidermis and Dermis The atopic dermatitis-induced lesion region of the animal model was analyzed to confirm the effect of tetrapeptide and ACP-tetrapeptide on atopic dermatitis. As a result, in the case of the epidermis, score level of group 2 was significantly higher than that of group 1 ($p<0.01$), and score levels of group 3, group 4 and group 5 were significantly lower than that of group 2 ($p<0.05$). In the case of the dermis, the score level of group 2 was significantly higher than that of group 1 ($p<0.01$), and the score levels of group 3, group 4 and group 5 were significantly lower than that of group 2 ($p<0.05$) (FIGS. 8 and 9).

In other words, the epidermal and dermal score levels of the tetrapeptide-treated group and the ACP-tetrapeptide treated group were lower than that of the induced control group, confirming the improvement effect of the tetrapeptide and ACP-tetrapeptide on the tissue of the atopic dermatitis lesion. Particularly, the ACP-tetrapeptide treated group showed a score similar to that of the normal control group for all the items, thereby confirming the superior inflammatory inhibitory effect of the ACP-tetrapeptide on the atopic dermatitis lesion of the epidermis and dermis.

1-6. Confirmation of Angiogenic Markers, Inflammatory Cell Distribution and Keratin Inhibitory Effect in Atopic Mouse Skin Tissues by Immunohistochemical Staining Analysis In order to examine the in vivo mechanism of tetrapeptide and ACP-tetrapeptide, angiogenesis markers, inflammatory cell distribution and keratin analysis in the atopic mouse skin tissues were performed.

Figure 10:
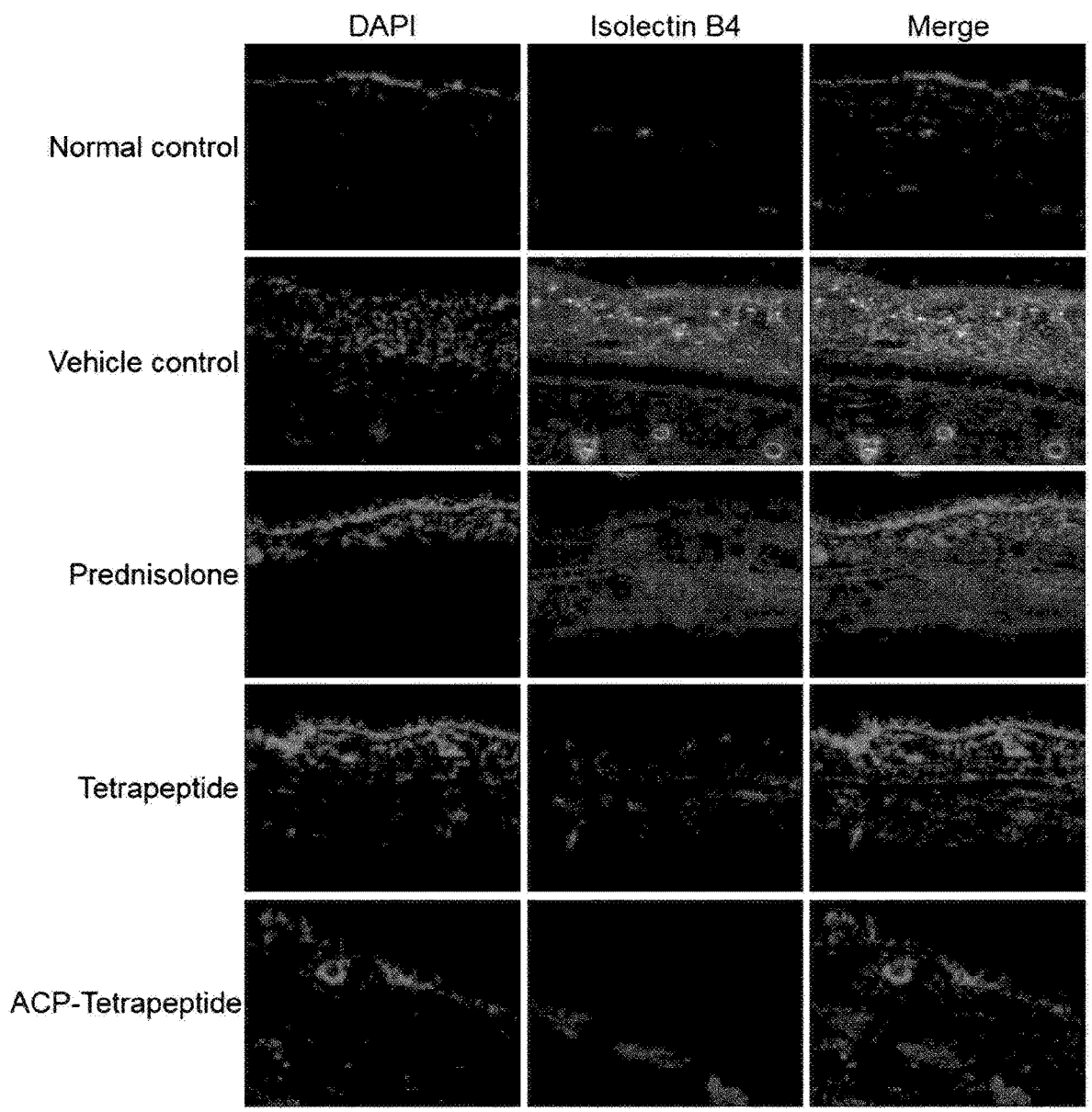
FIG. 10 is a photograph illustrating the results of fluorescence microscopy for the formation of blood vessels in skin tissue of mice having the atopic dermatitis.
Figure 11:
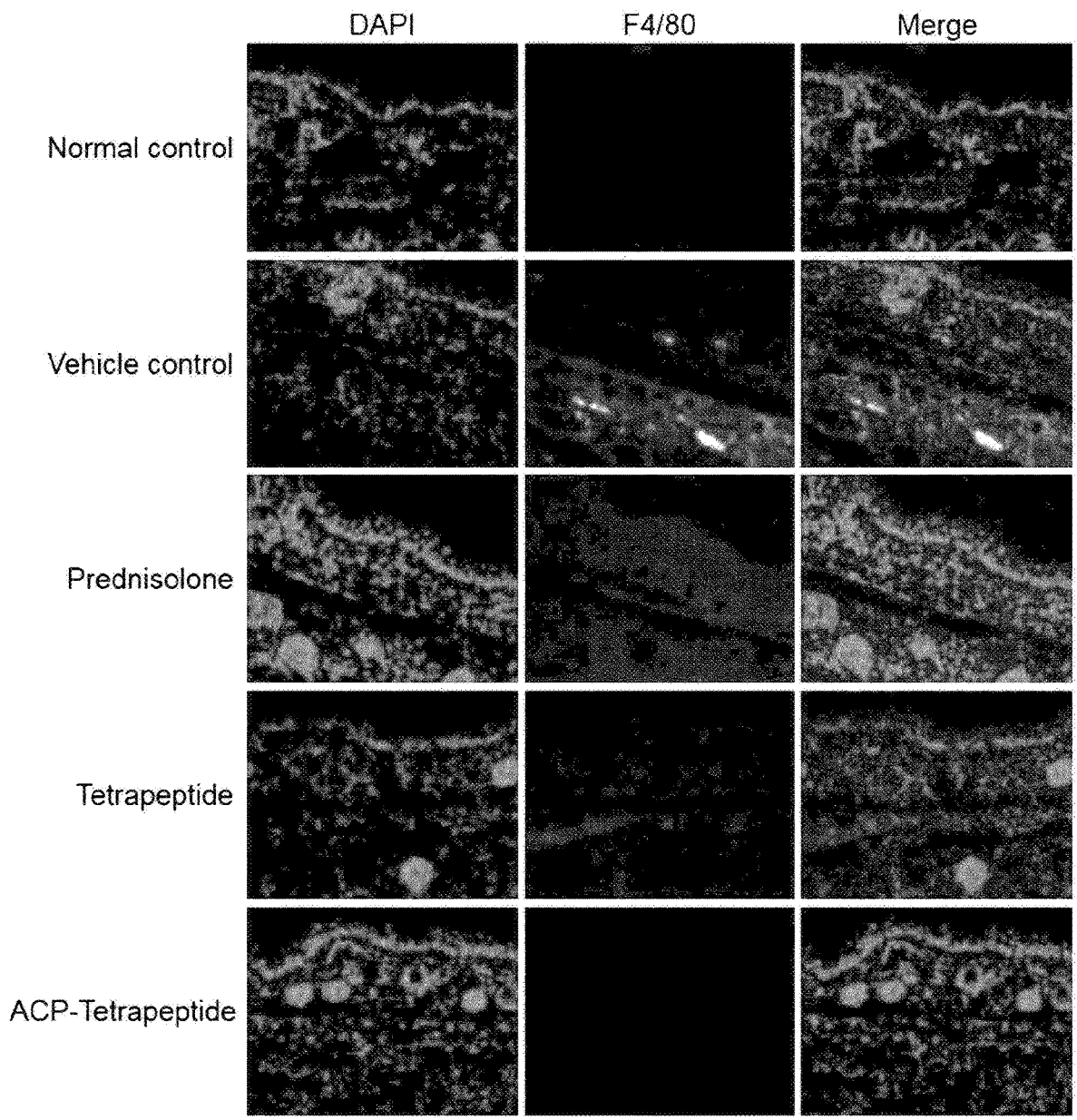
FIG. 11 is a photograph illustrating the results of fluorescence microscopy for the inflow of inflammatory cells in skin tissue of mice having the atopic dermatitis.
Figure 12:
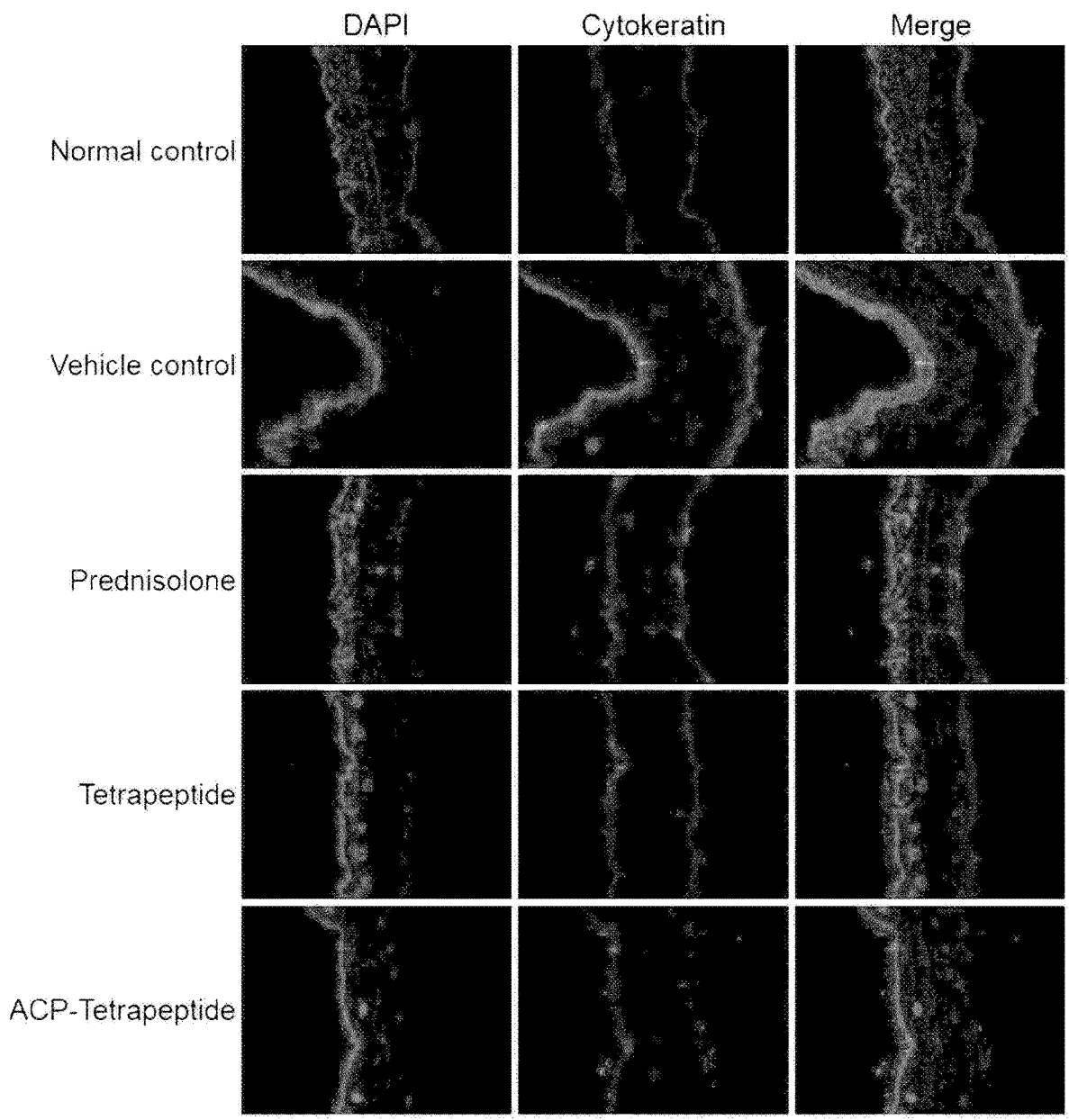
FIG. 12 is a photograph illustrating the results of fluorescence microscopy for the keratinization and fibrosis in skin tissue of mice having the atopic dermatitis.
Figure 13:
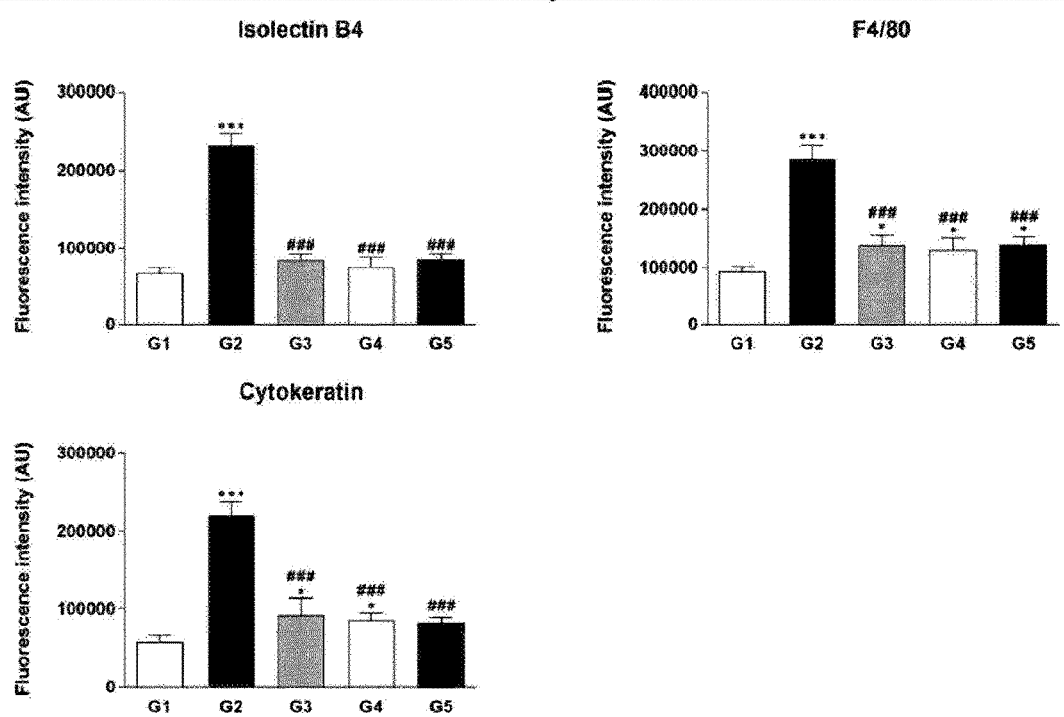
FIG. 13 is a graph illustrating immunohistochemical staining results of angiogenesis markers, inflammatory cells and keratins in skin tissue of mice having the atopic dermatitis.

As a result of staining the atopic mouse skin tissue with Isolectin B4, an angiogenesis marker, the angiogenesis of the tetrapeptide treated group and ACP-tetrapeptide treated group was lower than that of the inducted control group, which is similar to that of the prednisolone treated group (FIG. 10). As a result of staining the atopic mouse skin tissue with F4/80, an inflammatory cell marker, the inflammatory cell inflow of the tetrapeptide treated group and ACP-tetrapeptide treated group was lower than that of the inducted control group, which is similar to that of the prednisolone treated group (FIG. 11). As a result of staining the atopic mouse skin tissue with cytokeratins, keratinization and fibrosis markers, the keratinization and fibrosis of the tetrapeptide treated group and ACP-tetrapeptide treated group was lower than that of the inducted control group, which is similar to that of the prednisolone treated group (FIG. 12). The above results indicate that tetrapeptide and ACP-tetrapeptide inhibit angiogenesis and inflammatory cell inflow in atopic-induced dermal tissues as well as inhibit keratinization and fibrosis, thereby healing skin tissue of atopic dermatitis lesions. Further, as identified above, the tetrapeptide has the anti-atopic effect, which was confirmed by its treatment amount having a molar ratio lower than 1000 times that of prednisolone, and thus it was confirmed that the tetrapeptide has the superiority to prednisolone (FIG. 13).

2. Confirmation of Cell Membrane Permeability of ACP-Tetrapeptide

Figure 14:
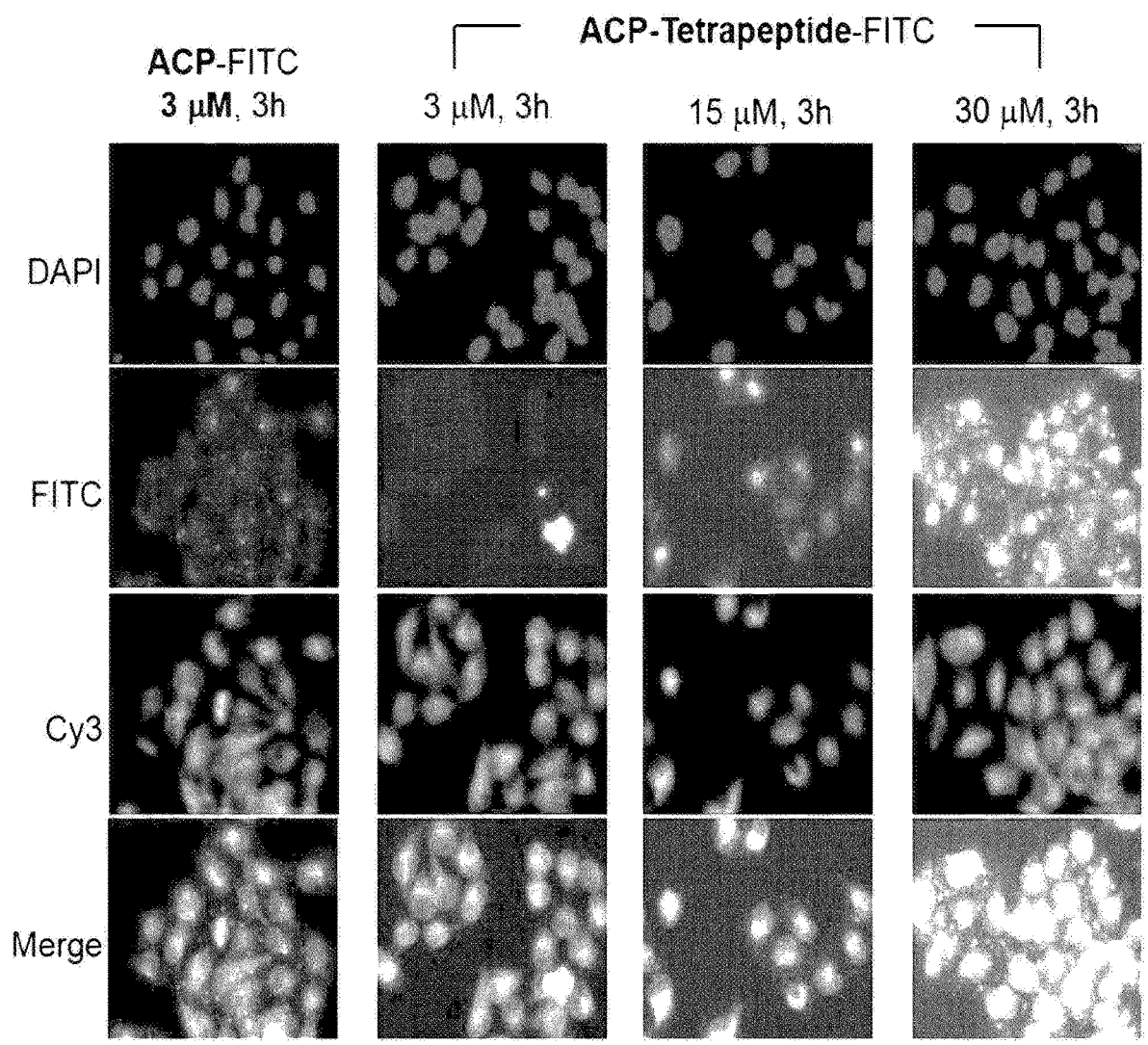
FIG. 14 is a fluorescence microscope photograph illustrating the cell permeability of the analyzed ACP-tetrapeptide.

In order to confirm the effect of ACP, which is a cell penetrating peptide, on the cell membrane permeability of ACP-tetrapeptide, fluorescence microscopic analysis was performed after transduction test in HeLa cell line. As a result, it was confirmed that the tetrapeptide was transferred into the cells through ACP in a concentration-dependent manner without aggregation in the cell membrane (FIG. 14). The above results indicate that when ACP-tetrapeptide is applied to the lesion of atopic dermatitis, ACP-tetrapeptide is efficiently delivered into the skin cells so that the skin inflammation is effectively inhibited in the epidermis as well as the dermis.

Figure 15:
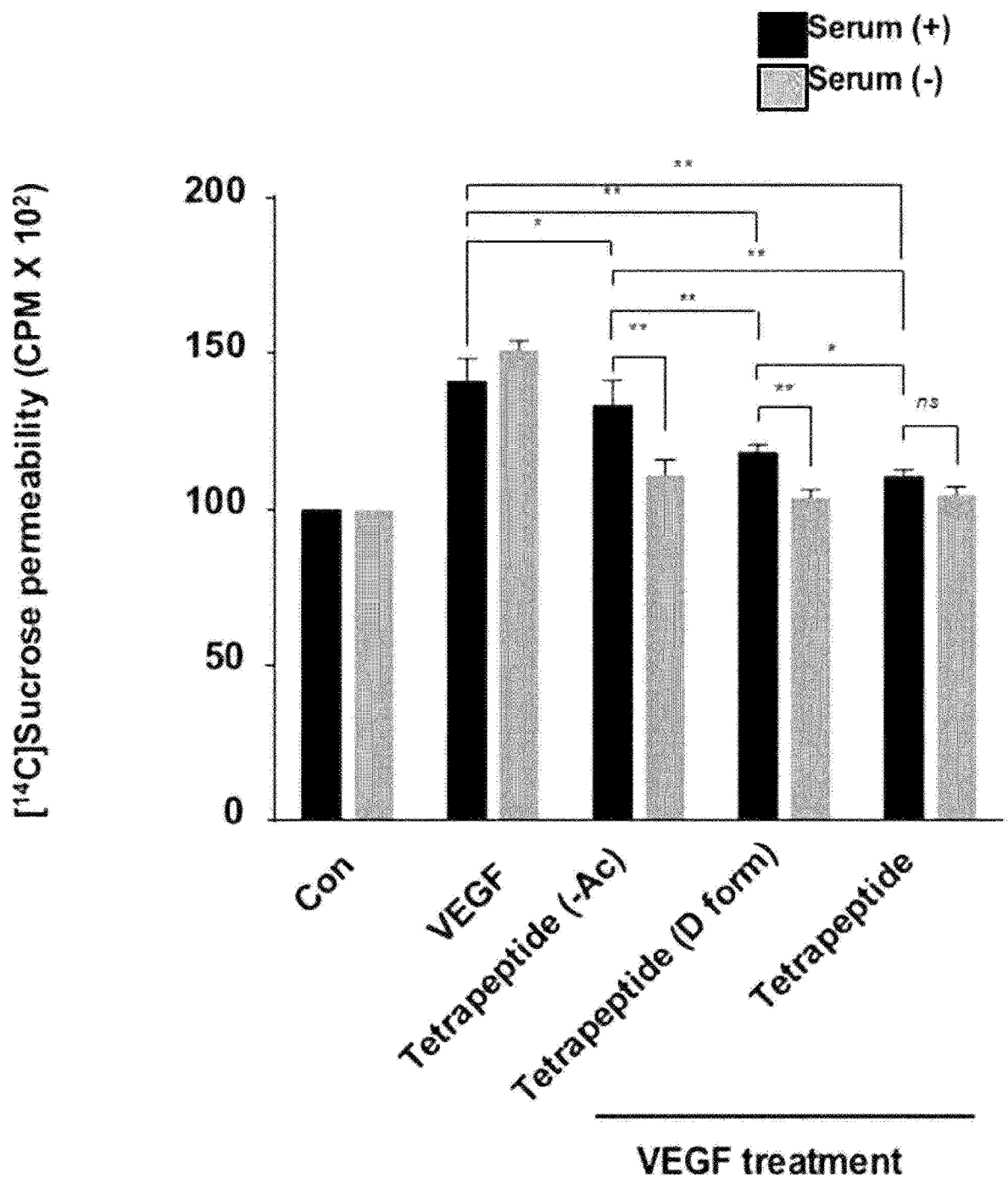
FIG. 15 is a graph illustrating the inhibitory effect of tetrapeptide on the vascular barrier permeability due to the vascular barrier breakdown.

3. Confirming the Inhibitory Effect of Tetrapeptide on Vascular Barrier Permeability Due to Vascular Barrier Breakdown 3-1. Confirming the Inhibitory Effect of Tetrapeptide on Increased Vascular Barrier Permeability Due to Vascular Barrier Breakdown in HUVE In order to confirm the inhibitory effect of tetrapeptides on increased vascular permeability due to the vascular barrier breakdown, HUVECs were treated with peptides and VEGF to measure vascular permeability. The results indicate that the acetylated tetrapeptides (denoted as Tetrapeptide), tetrapeptides in which Arg is a D-form (denoted as Tetrapeptide (D-form)) and non-acetylated tetrapeptides (denoted as Tetrapeptide (—Ac)) exhibited a similar level of inhibitory effect of vascular permeability as the control group without VEGF treatment (FIG. 15). In other words, it was confirmed from the above results that all three different types of tetrapeptides (acetylation, substitution with Arg having D-form, non-acetylation) can be applied to atopic dermatitis.

3-2. Confirming the Recovery Effect of Tetrapeptide on Levels of Tight Junction-Related Proteins Destroyed by VEGF in HUVEC Cell junction proteins must be present between cells in the vascular endothelial cells to tightly connect to each other, thereby inhibiting vascular permeability. Thus, it may prevent inflammatory cell migration in the vascular barrier. However, VEGF functions to damage cell junction proteins, thereby increasing the vascular permeability.

Figure 16:
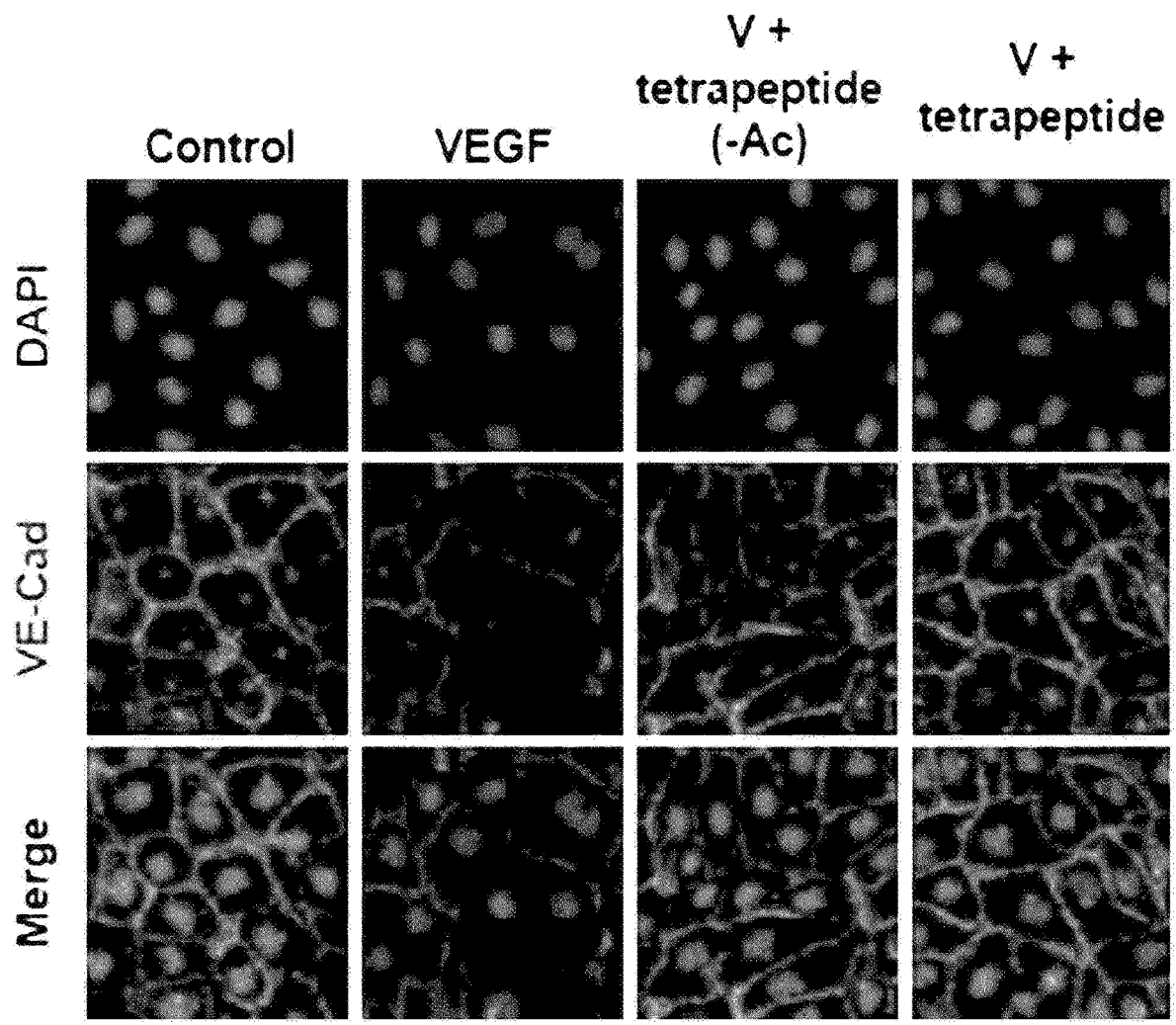
FIG. 16 is a confocal laser microscope (LSM 510 Meta, Carl Zeiss) photograph illustrating the recovery effect of tetrapeptide on the levels of VE-cad damaged by VEGF.
Figure 17:
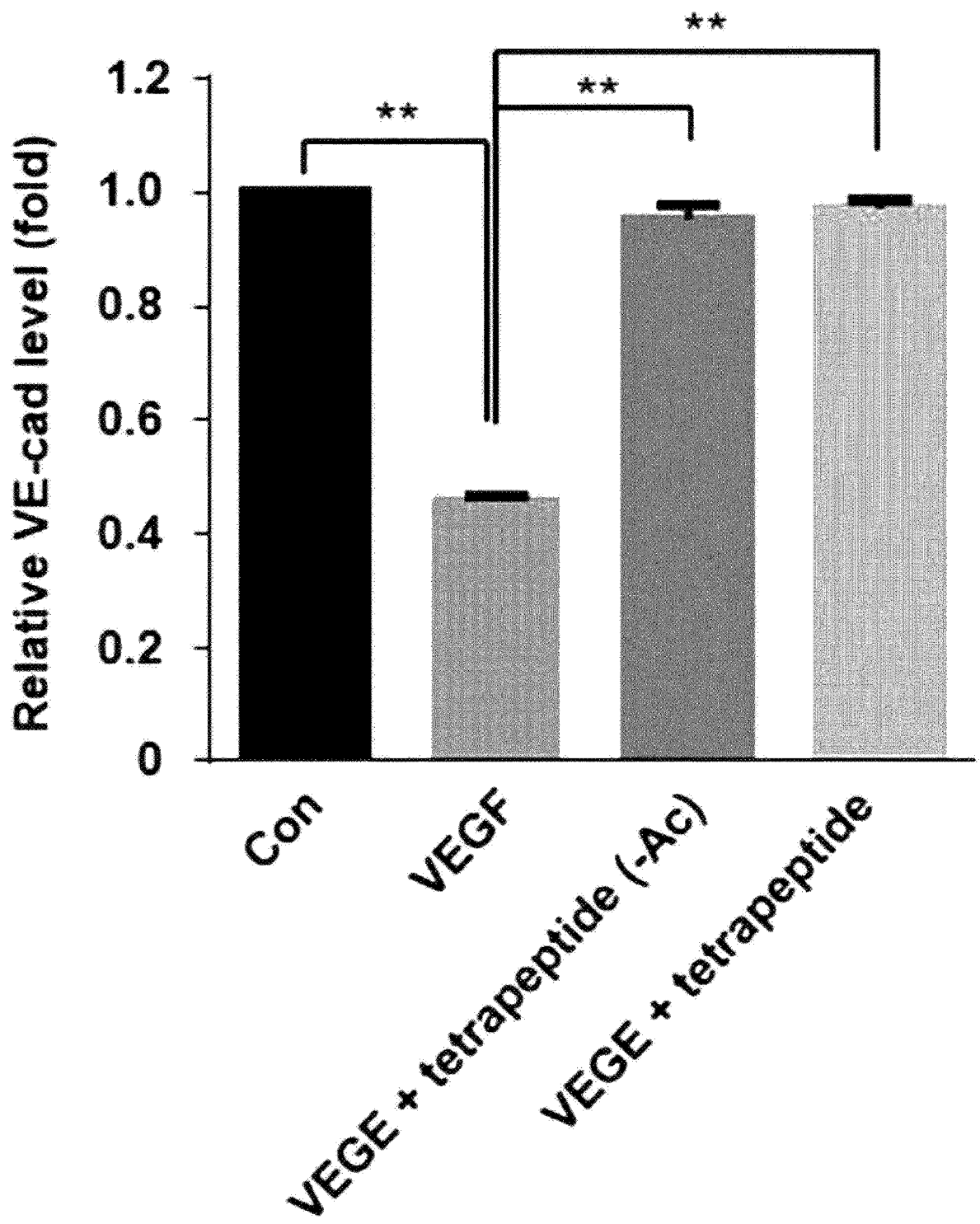
FIG. 17 is a graph illustrating the recovery effect of tetrapeptide on the levels of VE-cad damaged by VEGF.
Figure 18:
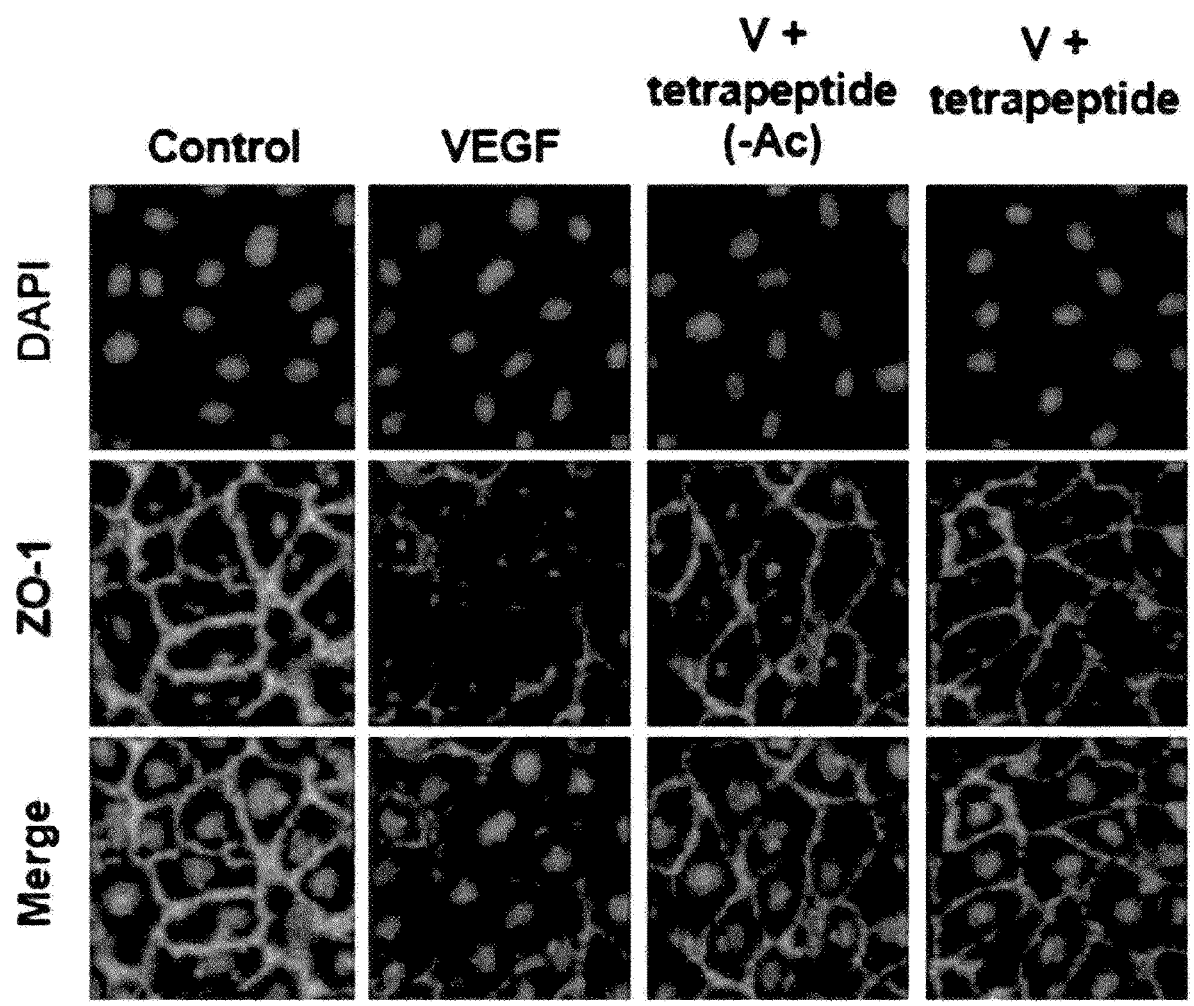
FIG. 18 is a confocal laser photograph illustrating the recovery effect of tetrapeptide on the levels of damaged by VEGF.
Figure 19:
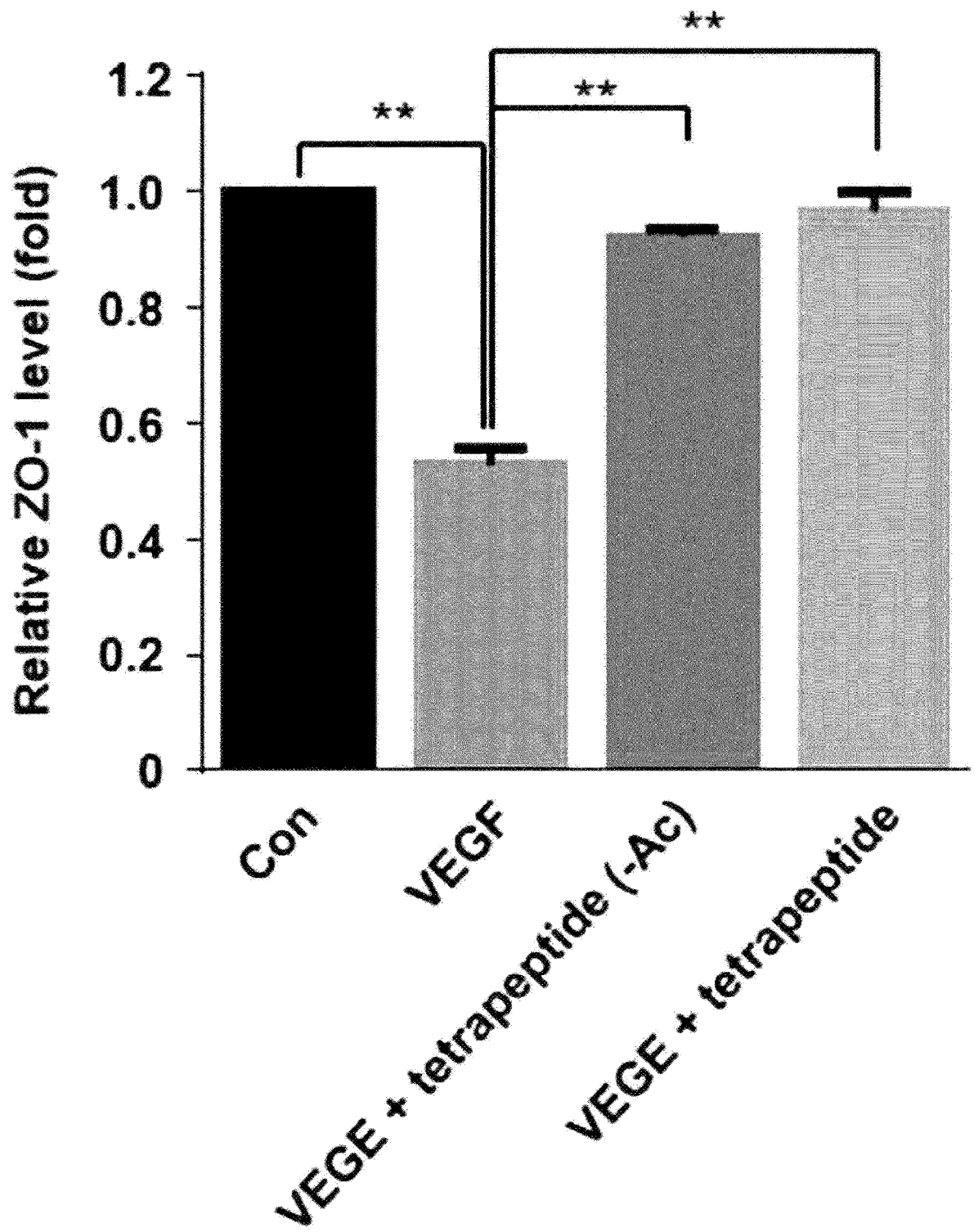
FIG. 19 is a graph illustrating the recovery effect of tetrapeptide on the levels of ZO-1 damaged by VEGF.

In order to confirm whether the tetrapeptides restore tight junction related proteins to inhibit the vascular barrier permeability, HUVECs were treated with peptides and VEGF to measure the permeability. As a result, because both acetylated and non-acetylated tetrapeptides blocked the signal of VEGFR-2, the damage levels of VE-cad (FIGS. 16 and 17) and ZO-1 (FIGS. 18 and 19) caused by VEGF were recovered to a level similar to that of the control group without VEGF treatment, resulting in a decrease in the vascular permeability. It was confirmed from the above results that both acetylated and non-acetylated tetrapeptides can be applied to atopic dermatitis.

As described above, the present invention has been described with reference to preferred embodiments thereof. It will be understood by those skilled in the art that various changes in form may be made therein without departing from the spirit and scope of the invention. Therefore, the disclosed embodiments should be considered in an illustrative rather than a restrictive sense. The scope of the present invention is indicated by the appended claims rather than by the foregoing description, and all differences within the scope of equivalents thereof should be construed as being included in the present invention.

The invention claimed is:

1. A method of treating atopic dermatitis comprising: administering an effective amount of a composition comprising a peptide consisting of the amino acid sequence represented by Arg-Leu-Tyr-Glu (SEQ ID NO:1) acetylated at the N-terminus to a subject in need thereof.

2. The method of claim 1, wherein the composition is a pharmaceutical composition.

3. The method of claim 2, wherein the composition is in a form selected from the group consisting of a gel, a paste, an ointment, a powder, an emulsion and an aerosol.

4. A method of treating atopic dermatitis or psoriasis comprising:
administering an effective amount of a composition comprising a peptide consisting of the amino acid sequence represented by Arg-Leu-Tyr-Glu (SEQ ID NO: 1) to a subject in need thereof,
wherein the peptide is linked to a cell penetrating peptide at N-terminal or C-terminal thereof.

5. The method of claim 4, wherein the cell penetrating peptide is selected from the group consisting of TAT, Antennapedia, VP22, Pep-1, polyarginine, poly-Lysine, Hph-1, Vectocell, Lactoferrin, Sim-2, LPIN3, 2IL-1a, and dNP2.

6. The method of claim 4, wherein the cell penetrating peptide is a polypeptide including the amino acid sequence represented by SEQ ID NO: 2.

7. The method of claim 4, wherein the composition is a pharmaceutical composition.

8. The method of claim 7, wherein the peptide is in a form selected from the group consisting of a gel, a paste, an ointment, a powder, an emulsion and an aerosol.

* * * * *